US009284274B2

(12) United States Patent
Kashman et al.

(10) Patent No.: US 9,284,274 B2
(45) Date of Patent: Mar. 15, 2016

(54) CHEMICAL DERIVATIVES OF JASMONATE, PHARMACEUTICAL COMPOSITIONS AND METHODS OF USE THEREOF

(71) Applicants: RAMOT AT TEL-AVIV UNIVERSITY LTD., Tel-Aviv (IL); SEPAL PHARMA LTD., Nes-Ziona (IL)

(72) Inventors: Yoel Kashman, Tel Aviv (IL); Eliezer Flescher, Hod Hasharon (IL); Max Herzberg, Sitrya (IL)

(73) Assignee: RAMOT at Tel-Aviv University Ltd., Tel Aviv (IL)

(*) Notice: Subject to any disclaimer, the term of this patent is extended or adjusted under 35 U.S.C. 154(b) by 301 days.

(21) Appl. No.: 13/831,766

(22) Filed: Mar. 15, 2013

(65) Prior Publication Data
US 2013/0203689 A1 Aug. 8, 2013

Related U.S. Application Data

(63) Continuation-in-part of application No. 12/095,908, filed as application No. PCT/IL2006/001408 on Dec. 7, 2006, now abandoned.

(60) Provisional application No. 60/742,875, filed on Dec. 7, 2005, provisional application No. 60/772,567, filed on Feb. 13, 2006.

(51) Int. Cl.
*A01N 43/42* (2006.01)
*A61K 31/47* (2006.01)
*C07D 215/12* (2006.01)
*C07D 215/14* (2006.01)
*C07D 215/24* (2006.01)
*C07H 13/04* (2006.01)
*C07D 215/32* (2006.01)

(52) U.S. Cl.
CPC ............ *C07D 215/24* (2013.01); *C07D 215/32* (2013.01); *C07H 13/04* (2013.01)

(58) Field of Classification Search
CPC ..... C07D 215/24; C07D 215/32; C07H 13/04
USPC .......................................... 514/311; 546/174
See application file for complete search history.

(56) References Cited

U.S. PATENT DOCUMENTS

| 3,932,389 | A | 1/1976 | Johnson |
| 3,951,876 | A | 4/1976 | Celli |
| 3,981,891 | A | 9/1976 | Celli |
| 4,154,949 | A | 5/1979 | Johnson |
| 5,476,945 | A | 12/1995 | Ikegawa |
| 5,637,484 | A | 6/1997 | Yukimune |
| 5,652,266 | A | 7/1997 | Bobier-Rival |
| 5,733,535 | A | 3/1998 | Hollingshead |
| 5,854,067 | A | 12/1998 | Newgard |
| 5,891,717 | A | 4/1999 | Newgard |
| 6,140,067 | A | 10/2000 | Anderson |
| 6,187,946 | B1 | 2/2001 | Fujisawa |
| 6,469,061 | B1 | 10/2002 | Flescher |
| 6,689,339 | B1 | 2/2004 | Tanaka |
| 6,861,431 | B2 | 3/2005 | Gudkov |
| 7,402,602 | B2 | 7/2008 | Bigg |
| 8,247,439 | B2 | 8/2012 | Herzberg |
| 8,481,594 | B2 | 7/2013 | Boulle |
| 2003/0219461 | A1 | 11/2003 | Britten |
| 2003/0224024 | A1 | 12/2003 | Leveque |
| 2004/0029839 | A1 | 2/2004 | Boulle |
| 2004/0081673 | A1 | 4/2004 | Rayner |
| 2004/0091493 | A1 | 5/2004 | Perrier |
| 2004/0116356 | A1 | 6/2004 | Malik |
| 2004/0116511 | A1 | 6/2004 | Malik |
| 2004/0180380 | A1 | 9/2004 | Lee |
| 2004/0259906 | A1 | 12/2004 | Altiok |
| 2005/0288210 | A1 | 12/2005 | Monteleone |
| 2006/0057558 | A1 | 3/2006 | Scott |
| 2006/0134237 | A1 | 6/2006 | Greene |
| 2006/0148732 | A1 | 7/2006 | Gutterman |
| 2007/0082852 | A1 | 4/2007 | Malik |
| 2008/0254055 | A1 | 10/2008 | Oblong |
| 2009/0064349 | A1 | 3/2009 | Goldstein |
| 2009/0197927 | A1 | 8/2009 | Herzberg |
| 2009/0197939 | A1 | 8/2009 | Walke |
| 2009/0252697 | A1 | 10/2009 | Barbarat |

(Continued)

FOREIGN PATENT DOCUMENTS

| CN | 1470494 | 1/2004 |
| CN | 102726514 | 10/2012 |

(Continued)

OTHER PUBLICATIONS

Abu-Hamad et al., (2008) Hexokinase-I protection against apoptotic cell death is mediated via interaction with the voltage-dependent anion channel-1: mapping the site of binding. J Biol Chem 283 (19): 13482-90.
Botham et al., (1998) Alternative methods for skin irritation testing: the current status. ECVAM Skin Irritation Task Force report 1. ATLA 26: 195-211.
Chen et al., (2007) The Warburg effect and its cancer therapeutic implications. J Bioenerg Biomembr 39 (3): 267-74.
Cotovio et al., (2005) The in vitro skin irritation of chemicals: optimization of the EpiSkin prediction model with the framework of the ECVAM validation process. ATLA 33: 329-49.
Flescher (2007) Jasmonates in cancer therapy. Cancer Lett 245 (1-2): 1-10.
Galluzzi et al., (2008) Disruption of the hexokinase-VDAC complex for tumor therapy. Oncogene 27(34): 4633-5.
Goldin et al., (2008) Methyl jasmonate binds to and detaches mitochondria-bound hexokinase: a new mechanism of cell death. Oncogene 27 (34): 4636-43.

(Continued)

*Primary Examiner* — Scarlett Goon
(74) *Attorney, Agent, or Firm* — Rodney J. Fuller; Booth Udall Fuller, PLC

(57) ABSTRACT

The present invention relates to novel jasmonate derivatives, methods for their preparation, pharmaceutical compositions including such compounds, and methods of using these compounds and compositions, especially as chemotherapeutic agents for prevention and treatment of cancers.

17 Claims, 5 Drawing Sheets

(56) References Cited

U.S. PATENT DOCUMENTS

| | | | |
|---|---|---|---|
| 2009/0291904 A1* | 11/2009 | Kashman et al. | 514/32 |
| 2010/0069497 A1 | 3/2010 | Boulle | |
| 2011/0245134 A1 | 10/2011 | Smets | |
| 2011/0245136 A1 | 10/2011 | Smets | |

FOREIGN PATENT DOCUMENTS

| | | |
|---|---|---|
| DE | 202012000163 | 1/2012 |
| EP | 0585104 | 3/1994 |
| EP | 0683232 | 11/1995 |
| EP | 1333021 | 8/2003 |
| FR | 2863893 | 6/2005 |
| FR | 2877222 | 5/2006 |
| GB | 1508169 | 4/1978 |
| JP | 63-122669 | 5/1988 |
| JP | 06-122653 | 5/1994 |
| JP | 7-308196 | 11/1995 |
| JP | 10029935 | 2/1998 |
| JP | 11-029412 | 2/1999 |
| JP | H11-139908 | 5/1999 |
| JP | H11-140022 | 5/1999 |
| JP | 2000-333691 | 12/2000 |
| JP | 2002205921 | 7/2002 |
| JP | 2003-238331 | 8/2003 |
| WO | 02/080890 | 10/2002 |
| WO | 2004/063155 | 7/2004 |
| WO | 2005/054172 | 6/2005 |
| WO | 2006/001021 | 1/2006 |
| WO | 2007/066337 | 6/2007 |
| WO | 2008/111088 | 9/2008 |
| WO | 2008/113495 | 9/2008 |
| WO | 2010/143180 | 12/2010 |
| WO | 2011000903 | 1/2011 |
| WO | 2011010075 | 1/2011 |

OTHER PUBLICATIONS

Gonzalez-Aguilar et al., (2001) Methyl jasmonate reduces chilling injury symptoms and enhances colour development of "Kent" mangoes. Jouranl of the Science of Food and Agriculture 81(13): 1244-1249.

Howes (1996) Method for assessing percutaneous absorption. The report and recommendation of ECVAM workshop 13. ATLA 24: 81-106.

Kniazhanski et al., (2008) Methyl jasmonate induces cell death with mixed characteristics of apoptosis and necrosis in cervical cancer cells. Cancer Letters, 271(1): 34-46.

Kondo and Fukuda (2001) Changes of jasmonates in grape berries and their possible roles in fruit development. Scientia Horticulturae 91(3,4): 275-288.

Kondo et al., (2004) Changes in Jasmonates of Mangoes during Development and Storage after Varying Harvest Times. Journal of the American Society for Horticultural Science 129(2): 152-157.

Kondo et al., (2005) Preharvest antioxidant activities of tropical fruit and the effect of low temperature storage on antioxidants and jasmonates. Postharvest Biology and Technology 36(3): 309-318.

Lalel et al., (2003) The role of methyl jasmonate in mango ripening and biosynthesis of aroma volatile compounds. Journal of Horticultural Science 78(4): 470-484.

Palmieri et al., (2011) A preliminary study of the local treatment of preneoplastic and malignant skin lesions using methyl jasmonate. Eur Rev Med Pharmacol Sci 15(3): 333-6.

Pastorino et al., (2005) Activation of glycogen synthase kinase 3β disrupts the binding of hexokinase II to mitochondria by phosphorylating voltage-dependent anion channel and potentiates chemotherapy-induced cytotoxicity. Cancer Res 65 (22): 10545-54.

Pedersen (2007) Warburg, me and Hexokinase 2: Multiple discoveries of key molecular events underlying one of cancers' most common phenotypes, the "Warburg Effect", i.e., elevated glycolysis in the presence of oxygen. J Bioenerg Biomembr 39 (3): 211-22.

Pedersen (2008) Voltage dependent anion channels (VDACs): a brief introduction with a focus on the outer mitochondrial compartment's roles together with hexokinase-2 in the "Warburg effect" in cancer. J Bioenerg Biomembr 40 (3): 123-6.

Pedersen et al., (2002) Mitochondrial bound type II hexokinase: a key player in the growth and survival of many cancers and an ideal prospect for therapeutic intervention. Biochim Biophys Acta 1555 (1-3): 14-20.

Rotem et al., (2003) The anticancer agent methyl jasmonate induces activation of stress-regulated c-Jun N-terminal kinase and p38 protein kinase in human lymphoid cells. Leukemia 17(11): 2230-56.

Saniewski et al., (1987) The effect of methyl jasmonate on ethylene and 1-amlnocyclopropane-l-carboxylic acid production in apple fruits. Biologia Plantarum 29(3): 199-203.

Scognamiglio et al., (2012) Fragrance material review on methyl jasmonate. Food and Chemical Toxicology 50 (suppl .): S572-576.

Shafiq et al., (2013) Time of methyl jasmonate application influences the development of 'Cripps Pink' apple fruit colour. Journal of the Science of Food and Agriculture 93(3): 611-618.

Tong et al., (2008) Methyl jasmonate downregulates expression of proliferating cell nuclear antigen and induces apoptosis in human neuroblastoma cells. Anti-Cancer Drugs 19(6): 573-81.

Wang et al., (2007) Society for Investigative Dermatology, 86th annual meeting: abstract ID 861.

Yeruva et al., (2006) Jasmonates induce apoptosis and cell cycle arrest in non-small cell lung cancer lines. Exp Lung Res 32 (10): 499-516.

Kang et al., (2013) Methyl 5-chloro-4,5-didehydrojasmonate (J7) inhibits macrophage-derived chemokine production via down-regulation of the signal transducers and activators of transcription 1 pathway in HaCaT human keratinocytes. Chem Pharm Bull (Tokyo) 61(10): 1002-8.

Michelet et al., (2012) The anti-ageing potential of a new jasmonic acid derivative (LR2412): in vitro evaluation using reconstructed epidermis Episkin™. Exp Dermatol 21(5): 398-400.

Weinges and Lernhardt (1990) Chemistry and Stereochemistry of Iridoids, XIII.—Synthesis of Enantiomerically Pure Methyl (1R,2S,2"Z)-(+)—Jasmonate Starting from Catapol. Liebigs Annalen Der Chemie 8: 751-4 (translated abstract).

Yoneyama et al., (1998) Effect of Jasmonates and Related Compounds on Seed Germination of Orobanche minor Smith and Striga hermonthica (Del.) Benth Biosci Biotechnol Biochem 62(7): 1448-50.

Zhao et al., (2004) Novel fluoro- and hydroxyl-containing jasmonate derivatives as highly efficient elicitors in suspension cultures of Taxus chinensis. Bioorg Med Chem Lett 14(18): 4755-8.

Miersch et al., (1987) Biological Activity of Jasmonic Acid Glucosyl Ester. Biochemie und Physiologie der Pflanzen 182 (5): 425-428.

Qian et al., (2004) Novel chemically synthesized hydroxyl-containing jasmonates as powerful inducing signals for plant secondary metabolism. Biotechnology and Bioengineering 86(7): 809-816.

Reischer-Pelech and Flescher (2012) Jasmonates: Plant Stress Hormones as Anticancer Agents. In: Emerging Trends in Dietary Components for Preventing and Combating Disease. Patil BS, Jayaprakasha GK, Murthy KNC, Seeram NP (Editors), ACS Symp Ser, Amer Chemical Society, Washington USA, pp. 303-322. Abstract.

Wang et al., (2005) Efficient elicitation of ginsenoside biosynthesis in cell cultures of Panax notoginseng by using self-chemically-synthesized jasmonates. Biotechnology and Bioprocess Engineering 10(2): 162-165.

Berge et al., (1977) Pharmaceutical Salts. J Pharm Sci 66(1): 1-19.

Bertrand et al., (2002) The BRET2/arrestin assay in stable recombinant cells: a platform to screen for compounds that interact with G protein-coupled receptors (GPCRS). J Recept Signal Transduct Res 22(1-4): 533-41.

Buchwald et al., (1980) Long-term, continuous intravenous heparin administration by an implantable infusion pump in ambulatory patients with recurrent venous thrombosis. Surgery 88: 507-16.

Davies ed., Plant Hormones, Kluwer Academic Publishers, London, 2004, pp. 618, 620.

(56) References Cited

OTHER PUBLICATIONS

Fingrut and Flescher (2002) Plant stress hormones suppress the proliferation and induce apoptosis in human cancer cells. Leukemia 16(4): 608-16.

Fingrut et al., (2005) Jasmonates induce nonapoptotic death in high-resistance mutant p53-expressing B-lymphoma cells. Br. J. Pharmacol. 146(6): 800-8.

Flescher (2005) Jasmonates—a new family of anti-cancer agents. Anticancer Drugs 16(9): 911-6.

Galluzzi et al., (2006) Mitochondria as therapeutic targets for cancer chemotherapy. Oncogene 25(34): 4812-30.

Goldin et al., (2007) Mitochondria-mediated ATP depletion by anti-cancer agents of the jasmonate family. J Bioenerg Biomembr 39(1): 51-7.

Hamon et al., (1975) Synthesis of prostanoic acid. Tetrahedron Lett 16(50): 4481-2.

Heyfets and Flescher (2007) Cooperative cytotoxicity of methyl jasmonate with anti-cancer drugs and 2-deoxy-D-glucose. Cancer Lett 250(2): 300-10.

Hossain et al., (2004) Fragrances in oolong tea that enhance the response of GABAA receptors. Biosci Biotechnol Biochem 68(9): 1842-8.

Ishii et al., (2004) Induction of differentiation of human myeloid leukemia cells by jasmonates, plant hormones. Leukemia 18(8): 1413-9.

Jikumaru et al., (2004) Preparation and biological activity of molecular probes to identify and analyze jasmonic acid-binding proteins. Biosci. Biotechnol. Biochem. 68(7): 1461-6.

Keinan et al., (2010) Oligomerization of the mitochondrial protein voltage-dependent anion channel is coupled to the induction of apoptosis. Mol Cell Biol 30(24): 5698-709.

Kim et al., (2004) Methyl jasmonate induces apoptosis through induction of Bax/Bcl-XS and activation of caspase-3 via ROS production in A549 cells. Oncol Rep 12(6): 1233-8.

Koda et al., (1991) Potato tuber-inducing activities of jasmonic acid and related compounds. Phytochemistry 30(5): 1435-8.

Kolho et al., (1993) Hepatitis C antibodies in dialysis patients and patients with leukaemia. J Med Virol 40(4): 318-21.

Kramell et al CAS: 111:39842 (1988).

Kramell et al., (1988) Synthesis of n-(jasmonoyl)amino acid conjugates. Tetrahedron 44(18): 5791-807.

Kramell et al., (1997) Chiral separation of amide conjugates of jasmonic acid by liquid chromatography. Chromatographia 45(1): 104-8.

Kuzuyama et al., (1999) Cloning and expression in *Escherichia coli* of 2-hydroxypropylphosphonic acid epoxidase from the fosfomycin-producing organism, Pseudomonas syringae PB-5123. Biosci Biotechnol Biochem 63(12): 2222-4.

Mathupala et al., (2006) Hexokinase II: cancer's double-edged sword acting as both facilitator and gatekeeper of malignancy when bound to mitochondria. Oncogene 25(34): 4777-86.

Mookherjee B.D. et al. (1974) International Congress of Essential Oils—CAS abstract AN1976:405236.

Morissette et al., (2004) High-throughput crystallization: Polymorphs, Salts, Co-crystals and solvates pharmaceutical solids. Advanced Drug Delivery Reviews 56(3): 275-300.

Ollivier and Salaun (1985) (±)-Dicranenone A from 1-hydroxycyclopropanecarboxaldehyde derivatives. J Chem Soc Chem Commun18: 1269-70.

Reischer et al., (2007) Effects of natural and novel synthetic jasmonates in experimental metastatic melanoma. Br J Pharmacol 150(6): 738-49.

Robey and Hay (2006) Mitochondrial hexokinases, novel mediators of the antiapoptotic effects of growth factors and Akt. Oncogene 25(34): 4683-96.

Rotem et al., (2005) Jasmonates: novel anticancer agents acting directly and selectively on human cancer cell mitochondria. Cancer Res 65(5): 1984-93.

Saudek et al., (1989) A preliminary trial of the programmable implantable medication system for insulin delivery. N. Eng J Med 321(9): 574-9.

Schneider et al., (1989) Separation of diastereomeric amino acid conjugates of jasmonic acid. Journal of Chromatography 483: 459-62.

Seto et al., (1992) Structure-Activity Relationships of (±)-Cucurbic Acid Analogs on the Root Growth of Rice Seedlings and Height of Young Corn Plants. Journal of Pesticide Science 17(1): 61-7.

Seto et al., (1999) Easy Preparation of Methyl 7-epi-Jasmonate and Four Stereoisomers of Methyl Cucurbate, and Assessment of the Stereogenic Effect of Jasmonate on Phytohormonal Activities. Biochem Biosc Biotech 63(2): 361-7.

Suemune et al., (1986) Conversion of Limonene to Prostanoic Acid and 8-Isoprostanoic Acid. Chemical and Pharmaceutical Bulletin 34(2): 550-7.

Suemune et al., (1987) Enzymatic Procedure for the Synthesis of 11-Deoxyprostaglandins. Chemical and Pharmaceutical Bulletin 35(5): 1741-7.

Taber and Malcolm (1998) Rhodium-Mediated Intramolecular C-H Insertion: Probing the Geometry of the Transition State. J Org Chem 63(11): 3717-21.

Ting and Morris, (1978) Reactivity of autolymphocytotoxic antibodies from dialysis patients with lymphocytes from chronic lymphocytic leukemia (CLL) patients. Transplantation 25(1): 31-3.

Ueda et al., (1981) Inhibitory effect of methyl jasmonate and its related compounds on kinetin-induced retardation of oat leaf senescence. Physiologia Plantarum 52(2): 305-9.

Vatela et al., (1988) Cyclic fatty acid monomers: synthesis and characterization of methyl ω-(2-alkylcyclopentyl) alkenoates and alkanoates. Chemistry and Physics of Lipids 48(1-2): 119-28.

Vippagunta et al., (2001) Crystalline solids. Adv Drug Deliv Rev 48(1): 3-26.

Wade, Jr., L.G. (1991) Organic Chemistry, 2nd edition. Published by Prentice-Hall, Inc., p. 952.

\* cited by examiner

CHEMICAL DERIVATIVES OF JASMONATE, PHARMACEUTICAL COMPOSITIONS AND METHODS OF USE THEREOF

RELATED U.S. APPLICATION DATA

This application is a continuation-in-part of application Ser. No. 12/095,908, filed Sep. 23, 2008, which is the U.S. National Phase of International Application No. PCT/IL2006/001408 on Dec. 7, 2006, which claims the benefit of U.S. Provisional Application No. 60/742,875, filed on Dec. 7, 2005, and U.S. Provisional Application No. 60/772,567, filed on Feb. 13, 2006. The entire content of each listed application is expressly incorporated herein by reference thereto.

FIELD OF THE INVENTION

The present invention relates to the field of jasmonate derivative compounds, methods for their preparation, pharmaceutical compositions including such compounds, and methods of using these compounds and compositions, especially as chemotherapeutic agents for treatment of cancers especially in mammals, and particularly in humans.

BACKGROUND OF THE INVENTION

Jasmonates are a family of plant stress hormones, derived from linolenic acid by the octadecanoid pathway, which are found in minute quantities in many edible plants. Stress hormones such as the jasmonate family have evolved in plants, and are released in such times of stress such as extreme UV radiation, osmotic shock, heat shock and pathogen attack, to initiate various cascades which end in appropriate responses. Examples of members of the jasmonate family are jasmonic acid, which is crucial to intracellular signaling in response to injury, and methyl jasmonate, which causes induction of a proteinase inhibitor that accumulates at low concentrations in response to wounding or pathogenic attacks. Use of jasmonates for the treatment of mammalian cancer has been disclosed in U.S. Pat. No. 6,469,061, the contents of which are incorporated by reference in their entirety. In U.S. Pat. No. 6,469,061, it was shown that jasmonates were directly cytotoxic for various types of human cancer cells derived from breast, prostate, skin and blood cancers. While jasmonates elicited death in human leukemic Molt-4 cells, they did not damage normal lymphocytes.

In U.S. Pat. No. 6,469,061, one jasmonate compound in particular, methyl jasmonate, was shown to be effective in preventing development of lymphomas in mice. See also Fingrut, O. and E. Flescher. 2002. "Plant stress hormones suppress the proliferation and induce apoptosis in human cancer cells", Leukemia 16: 608-616 (2002).

Subsequent data collected similarly showed that jasmonates do not damage healthy erythrocytes (see WO 02/080890, the contents of which are incorporated by reference in their entirety).

PCT International Patent Publication WO 2005/054172 discloses novel halogenated jasmonate derivatives, pharmaceutical compositions comprising the derivatives, and their use for reducing cancer cell growth and for treating cancer.

Jasmonic acids conjugated via the carboxyl group to amino acids occur in nature (Plant Hormones, Davies P J, ed., Kluwer Academic Publishers, London, 2004, pp. 618, 620). Several jasmonic acid-amino acid conjugates have been synthetically prepared. The amino acids include glycine, alanine, valine, leucine and isoleucine. (Jikumaru Y. et al. Biosci. Biotechnol. Biochem. 68, 1461-1466, 2004).

The pharmacological activity of jasmonate compounds makes them attractive candidates as therapeutic agents for the treatment of cancer. Only very few jasmonate derivatives have been reported in the art (see, for example, Ishii et al., Leukemia, 1-7 (2004); Seto et al. Biochem. Biosc. & Biotech. 63(2), (1999); Hossain et al. Biochem. Biosci. & Biotech. 68(9), 1842, (2004)). An unmet need exists to develop jasmonate derivative compounds that are potent chemotherapeutic drugs, with a high degree of specificity towards malignant cells.

SUMMARY OF THE INVENTION

The present invention relates to novel jasmonate derivative compounds. Preferred jasmonate derivatives are represented by the general structure of formula II. Other preferred jasmonate derivatives are specific derivatives represented by the structures 9, 9A 12 and 13. Several of these compounds are significantly more potent than the compounds disclosed in U.S. Pat. No. 6,469,061 and WO 2005/054172. The novel derivatives exert selective cytotoxicity on cancerous cells, while sparing normal cells. As such, the compounds of the present invention are useful in inhibiting cancer cell proliferation and treating a variety of cancers.

In one embodiment, the jasmonate derivatives are represented by the structure of formula II.

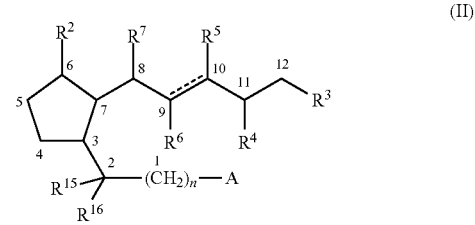

wherein
A is COR$^1$;
R$^1$ is a heteroaryloxy;
R$^2$ is selected from the group consisting of hydrogen, unsubstituted or substituted C$_1$-C$_{12}$ alkyl, unsubstituted or substituted C$_3$-C$_8$ cycloalkyl, unsubstituted or substituted aryl, unsubstituted or substituted heteroaryl, OR$^8$, oxo and NR$^{9a}$R$^{9b}$;
R$^3$, R$^4$, R$^5$, R$^6$ and R$^7$ are each independently selected from the group consisting of hydrogen, unsubstituted or substituted C$_1$-C$_{12}$ alkyl, unsubstituted or substituted C$_1$-C$_{12}$ haloalkyl, unsubstituted or substituted C$_3$-C$_8$ cycloalkyl, unsubstituted or substituted aryl, unsubstituted or substituted heteroaryl, OR$^8$ and NR$^{9a}$R$^{9b}$,
or R$^5$ and R$^6$ together with the carbons to which they are attached form a C$_3$-C$_8$ cycloalkyl or a C$_3$-C$_8$ cycloalkyl substituted by halo;
or one of R$^5$ and R$^6$ represents an oxygen atom which is bonded to C$_6$, thereby forming an oxygen-containing 6 or 5 membered heterocyclic ring, respectively;
wherein the bond between C$_9$ and C$_{10}$ can be a single or double bond;
R$^8$, R$^{9a}$ and R$^{9b}$ are each independently selected from the group consisting of hydrogen, unsubstituted or substituted C$_1$-C$_{12}$ alkyl, unsubstituted or substituted C$_3$-C$_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S;

$R^{15}$ and $R^{16}$ are each independently selected from the group consisting of hydrogen and unsubstituted or substituted $C_1$-$C_4$ alkyl;

n is selected from 0, 1 and 2; including salts, hydrates, solvates, polymorphs, optical isomers, geometrical isomers, enantiomers, diastereomers, and mixtures thereof.

In one currently preferred embodiment, the group A in formula II is $COR^1$. In one embodiment, $R^1$ heteroaryloxy, preferably quinolinyloxy.

In one currently preferred embodiment, $R^2$ in formula II is oxo (=O). In another currently preferred embodiment, $R^2$ in formula II is $OR^8$ wherein $R^8$ is an unsubstituted or substituted $C_1$-$C_{12}$ alkyl, e.g., methyl.

In one currently preferred embodiment, $R^5$ and $R^6$ together with the carbons to which they are attached (i.e., $C_9$ and $C_{10}$) form an unsubstituted $C_3$-$C_8$ cycloalkyl or a $C_3$-$C_8$ cycloalkyl substituted by one or more halogen atoms. In one specific embodiment, $R^5$ and $R^6$ together represent a $C(Hal)_2$ group wherein Hal is halogen, and together with $C_9$ and $C_{10}$ define a halo-substituted cyclopropyl group.

In another embodiment, each of $R^3$, $R^4$, $R^5$, $R^6$ and $R^7$ is hydrogen. In another embodiment, the bond between $C_9$ and $C_{10}$ is a double bond, and each of $R^3$, $R^4$, $R^5$, $R^6$ and $R^7$ is hydrogen. In yet another embodiment, the bond between $C_9$ and $C_{10}$ is a single bond, and each of $R^3$, $R^4$, $R^5$, $R^6$ and $R^7$ is hydrogen. In yet another embodiment, $R^6$ represents an oxygen atom which is bonded to $C_6$, thereby forming an oxygen-containing 5 membered heterocyclic ring.

Specific examples of the compounds of formula II include but are not limited to:

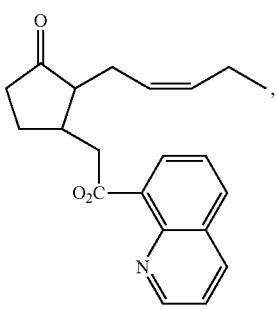

9

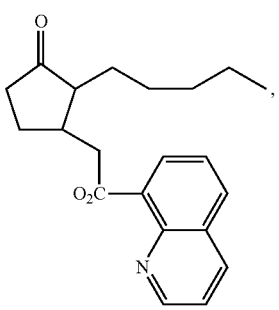

9A

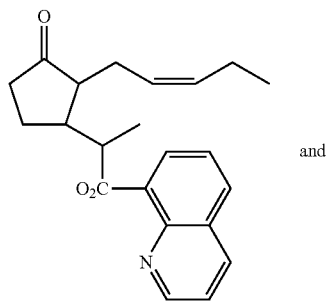

12 and

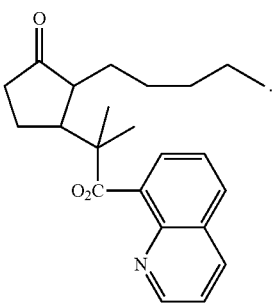

13

The present invention also contemplates pharmaceutical compositions that include a pharmaceutically acceptable carrier and, as an active ingredient, one or more of the compounds of the invention, represented by any of general formula II or by any of the specific compounds of formulas 9, 9A, 12 and 13, as described above.

The pharmaceutical compositions of the present invention can be provided in any form known in the art, for example in a form suitable for oral administration (e.g., a solution, a suspension, a syrup, an emulsion, a dispersion, a suspension, a tablet, a pill, a capsule, a pellet, granules and a powder), for parenteral administration (e.g., intravenous, intramuscular, intraarterial, transdermal, subcutaneous or intraperitoneal), for topical administration (e.g., an ointment, a gel, a cream), for administration by inhalation or for administration via suppository. Preferably, in the pharmaceutical composition of the present invention, the active ingredient is dissolved in any acceptable lipid carrier.

Further, in accordance with a preferred embodiment of the present invention, the jasmonate derivatives are administered together with at least one other chemotherapeutic agent. The jasmonate derivative and the at least other chemotherapeutic agent can be administered simultaneously (in the same or in separate dosage forms), or they can be administered sequentially, in any order.

The present invention additionally provides a method for inhibiting cancer cell proliferation, comprising contacting the cancer cells with a therapeutically effective amount of a compound of any of general formula II, or of formulas 9, 9A, 12 and 13 as described herein. In some embodiments, the compound is administered in a pharmaceutical composition.

Furthermore, the present invention provides a method for the treatment of cancer in a subject, by administering to the subject a therapeutically effective amount of the compound of the invention, as described herein. Preferably, the compound is one or more of the compounds represented by any of general formula II or by any of the specific formulas 9, 9A, 12 and 13. In some embodiments, the compound is administered in a pharmaceutical composition. In one embodiment, the subject is a mammal, preferably a human.

Furthermore, the present invention relates to the use of a compound of any of formulas II, 9, 9A, 12 or 13 according to the present invention in the preparation of a medicament useful for the treatment of cancer.

The compounds of the present invention are active against a wide range of cancers, including carcinomas, sarcomas, myelomas, leukemias, lymphomas and mixed type tumors. Particular categories of tumors amenable to treatment include lymphoproliferative disorders, breast cancer, ovarian cancer, prostate cancer, cervical cancer, endometrial cancer, bone cancer, liver cancer, stomach cancer, colon cancer, pancreatic cancer, cancer of the thyroid, head and neck cancer, cancer of the central nervous system, cancer of the peripheral nervous system, skin cancer, kidney cancer, as well as metastases of all the above. Particular types of tumors amenable to treatment include: hepatocellular carcinoma, hepatoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, melanoma, squamous cell carcinoma, basal cell carcinoma, adenocarcinoma (well differentiated, moderately differentiated, poorly differentiated or undifferentiated), renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, astrocyoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma.

According to certain embodiments, the cancer to be treated is selected from the group consisting of prostate cancer, breast cancer, skin cancer, colon cancer, lung cancer, pancreatic cancer, lymphoma, leukemia, myeloma, head and neck cancer, kidney cancer, ovarian cancer, bone cancer, liver cancer or thyroid cancer. According to exemplary embodiments, the cancer to be treated is selected from breast cancer, kidney cancer, stomach cancer, leukemia, including lymphoblastic leukemia, lung carcinoma, melanoma and colon cancer.

The jasmonate derivatives of the present invention are significantly more potent than the compounds disclosed in U.S. Pat. No. 6,469,061 and WO 2005/054172. They display an unexpected cytotoxic effect with a high degree of specificity towards malignant cells.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PRESENT INVENTION

Figure 1A:
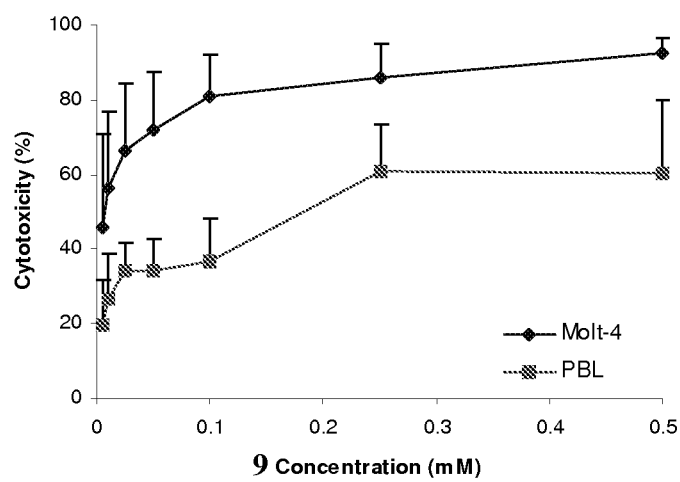
FIG. 1: Shows the cytotoxic activity of increasing concentrations (0.01-0.5 mM) of compounds 9 (FIG. 1A) and 11 (FIG. 1B) in lymphoblastic leukemia cells (Molt-4) and peripheral blood lymphocytes (PBL). Cytotoxicity (%) is plotted against the compound concentration.

The present invention relates to novel jasmonate derivative compounds. Preferred jasmonate derivatives are represented by the general structure of formulae I and II. Other preferred jasmonate derivatives are specific derivatives represented by the structures 1-13. Some of these compounds are significantly more potent than the compounds disclosed in the art, and exert selective cytotoxicity on cancerous cells, e.g. lymphocytes, carcinoma cells and breast cancer cells, while having very low effect on normal cells. As such, the compounds of the present invention are useful in inhibiting cancer cell proliferation and treating a variety of cancers.

In one embodiment, the compounds of the present invention are jasmonate derivatives represented by the general structure of formula I:

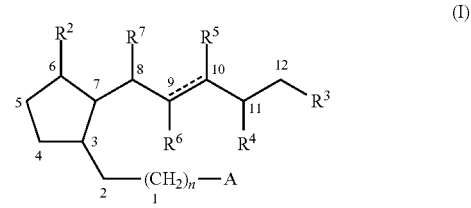

wherein
A is selected from the group consisting of:
a) $COR^1$;
b) $O-COR^{16}$; and
c) $OR^{11}$;

$R^1$ is selected from the group consisting of
a) heteroaryloxy;
b) $-O[(CH_2)_pO]_m-R^{12}$;
c) a group of the formula:

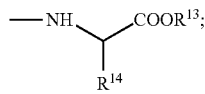

and d) when at least one of $R^3$, $R^4$, $R^5$, $R^6$ and $R^7$ is haloalkyl or when $R^5$ and $R^6$, together with the carbons to which they are attached form a $C_3$-$C_8$ cycloalkyl or a $C_3$-$C_8$ cycloalkyl substituted by halo, $R^1$ can further represent hydrogen or unsubstituted or substituted $C_1$-$C_{12}$ alkyl;

$R^2$ is selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, oxo and $NR^{9a}R^{9b}$;

$R^3$, $R^4$, $R^5$, $R^6$ and $R^7$ are each independently selected from the group consisting of hydrogen, halogen, unsubstituted or substituted $C_1$-$C_{12}$ alkyl, unsubstituted or substituted $C_1$-$C_{12}$ haloalkyl, unsubstituted or substituted $C_3$-$C_8$ cycloalkyl, unsubstituted or substituted aryl, unsubstituted or substituted heteroaryl, $OR^8$ and $NR^{9a}R^{9b}$, or $R^5$ and $R^6$ together with the carbons to which they are attached form a $C_3$-$C_8$ cycloalkyl or a $C_3$-$C_8$ cycloalkyl substituted by halo;

or one of $R^5$ and $R^6$ represents an oxygen atom which is bonded to $C_6$, thereby forming an oxygen-containing 6 or 5 membered heterocyclic ring, respectively;

wherein the bond between $C_9$ and $C_{10}$ can be a single or double bond;

$R^8$, $R^{9a}$ and $R^{9b}$ are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S;

$R^{10}$ is selected from the group consisting of hydrogen, unsubstituted or substituted $C_1$-$C_{12}$ alkyl, unsubstituted or substituted $C_3$-$C_8$ cycloalkyl, unsubstituted or substituted aryl and unsubstituted or substituted heteroaryl;

$R^{11}$ and $R^{12}$ are each independently hydrogen or a hydroxy protecting group;

$R^{13}$ is a carboxy protecting group;

$R^{14}$ is the residue of a natural or unnatural amino acid;

n is selected from 0, 1 and 2;

m is an integer of 1 to 20; and p is an integer of 1 to 12;

including salts, hydrates, solvates, polymorphs, optical isomers, geometrical isomers, enantiomers, diastereomers, and mixtures thereof.

In another embodiment, the jasmonate derivatives are represented by the structure of formula II.

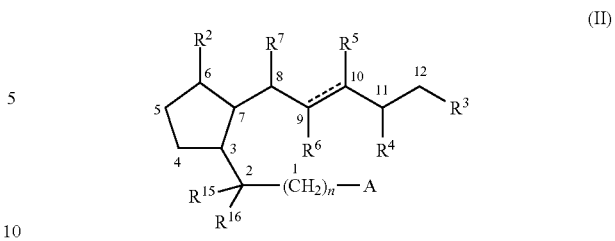

wherein

A is $COR^1$;

$R^1$ is a heteroaryloxy;

$R^2$ is selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, oxo and $NR^{9a}R^{9b}$;

$R^3$, $R^4$, $R^5$, $R^6$ and $R^7$ are each independently selected from the group consisting of hydrogen, unsubstituted or substituted $C_1$-$C_{12}$ alkyl, unsubstituted or substituted $C_1$-$C_{12}$ haloalkyl, unsubstituted or substituted $C_3$-$C_8$ cycloalkyl, unsubstituted or substituted aryl, unsubstituted or substituted heteroaryl, $OR^8$ and $NR^{9a}R^{9b}$, or $R^5$ and $R^6$ together with the carbons to which they are attached form a $C_3$-$C_8$ cycloalkyl or a $C_3$-$C_8$ cycloalkyl substituted by halo;

or one of $R^5$ and $R^6$ represents an oxygen atom which is bonded to $C_6$, thereby forming an oxygen-containing 6 or 5 membered heterocyclic ring, respectively;

wherein the bond between $C_9$ and $C_{10}$ can be a single or double bond;

$R^8$, $R^{9a}$ and $R^{9b}$ are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S;

$R^{15}$ and $R^{16}$ are each independently selected from the group consisting of hydrogen and unsubstituted or substituted $C_1$-$C_4$ alkyl;

n is selected from 0, 1 and 2;

including salts, hydrates, solvates, polymorphs, optical isomers, geometrical isomers, enantiomers, diastereomers, and mixtures thereof.

In one currently preferred embodiment, the group A in formula I or formula II is $COR^1$. In one embodiment, $R^1$ heteroaryloxy, i.e. a heteroaryl moiety as described herein, linked to an oxygen. A currently preferred heteroaryloxy group is a quinolinyloxy group. The heteroaryloxy group may be substituted or unsubstituted, with each possibility representing a separate embodiment of the present invention.

In another embodiment, the group A in formula I or formula II is $COR^1$ and $R^3$, $R^4$, $R^5$, $R^6$ and $R^7$ are each independently selected from the group consisting of hydrogen, unsubstituted or substituted $C_1$-$C_{12}$ alkyl, unsubstituted or substituted $C_1$-$C_{12}$ haloalkyl, unsubstituted or substituted $C_3$-$C_8$ cycloalkyl, unsubstituted or substituted aryl, unsubstituted or substituted heteroaryl, $OR^8$ and $NR^{9a}R^{9b}$. Each possibility represents a separate embodiment of the invention.

In another embodiment, the group A in formula I is $COR^1$ and $R^1$ is a polyoxyalkylene represented by the structure $-O[(CH_2)_pO]_m-R^{12}$, wherein m and p are as described above for formula I. For example, a polyoxyalkylene group can be a polyoxy $C_1$-$C_{12}$ alkylene, i.e., when p is an integer of 1 to 12. A non-limiting example of a polyoxy $C_1$-$C_{12}$ alkylene is polyethyleneglycol represented by the structure-O(CH$_2$—CH$_2$—O)$_m$— wherein m is an integer of 1 to 20. A currently preferred value for m is 4. The group $R^{12}$ represents hydrogen or a hydroxy protecting group. Any hydroxy protecting group described herein or known to a person of skill in the art can be used, for example a silyl group (e.g., trialkylsilyl, triarylsilyl, dialkyaryllsilyl, diarylalkylsilyl and the like), $C_1$-$C_4$ alkyl, —CO—($C_1$-$C_6$ alkyl), —SO$_2$—($C_1$-$C_6$ alkyl), —SO$_2$—Ar, —CO—Ar wherein Ar is an aryl group as defined herein, and —CO—($C_1$-$C_6$ alkyl)Ar (e.g., a carboxybenzyl group). A currently preferred hydroxy protecting group for $R^{12}$ is a silyl protecting group such as a trialkylsilyl protecting group (e.g., t-butyldimethylsilyl).

In another embodiment, the group A in formula I is $COR^1$ and $R^1$ is a group of the formula:

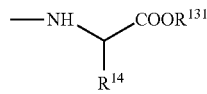

The group $R^{13}$ can be any carboxy protecting group, for example alkyl, e.g. methyl, ethyl, propyl, isopropyl, butyl, isobutyl, sec-butyl, t-butyl, pentyl, 2-pentyl, 3-pentyl and the like. The group $R^{14}$ represents the residue of any natural or unnatural amino acid. Any natural and unnatural amino acid defined herein and known to a person of skill in the part can be incorporated into the jasmonate-amino acid derivatives of the present invention In another currently preferred embodiment, the group A in formula I is O—$COR^{10}$, wherein $R^{10}$ is an unsubstituted or substituted $C_1$-$C_{12}$ alkyl, for example methyl, ethyl, propyl, isopropyl, butyl, isobutyl, sec-butyl, t-butyl, pentyl, 2-pentyl, 3-pentyl and the like. In yet another currently preferred embodiment, the group A in formula I is $OR^{11}$ wherein $R^{11}$ is hydrogen or a hydroxy protecting group as defined above. A currently preferred hydroxy protecting group for $R^{11}$ is a silyl protecting group such as a trialkylsilyl protecting group (e.g., t-butyldimethylsilyl).

In one currently preferred embodiment, $R^2$ in formula I or formula II is oxo (=O). In another currently preferred embodiment, $R^2$ in formula I or formula II is $OR^8$ wherein $R^8$ is an unsubstituted or substituted $C_1$-$C_{12}$ alkyl, e.g., methyl, ethyl, propyl, isopropyl, butyl, isobutyl, sec-butyl, t-butyl, pentyl, 2-pentyl, 3-pentyl and the like.

In one currently preferred embodiment, $R^5$ and $R^6$ together with the carbons to which they are attached (i.e., $C_9$ and $C_{10}$) form an unsubstituted or substituted $C_3$-$C_8$ cycloalkyl. Preferred substituents for the $C_3$-$C_8$ cycloalkyl is $C_1$-$C_{12}$ alkyl or halogen. For example, for purposes of illustration and not for limitation, $R^5$ and $R^6$ can together define a (CRR')$_a$ group wherein each of R and R' is independently a hydrogen, $C_1$-$C_{12}$ alkyl or halogen and "a" is an integer of 1-6, thereby forming a 3-8 cyclic ring together with $C_9$ and $C_{10}$. In one specific embodiment, $R^5$ and $R^6$ together represent a C(Hal)$_2$ group wherein Hal is halogen, and together with $C_9$ and $C_{10}$ define a halo-substituted cyclopropyl group. Also, as apparent to a person of skill in the art, any other substituents, together with the carbons to which they are attached, can similarly form a 3-8 membered cyclic structures. For example, any of the groups $R^3$ and $R^4$; $R^3$ and $R^5$; $R^3$ and $R^6$; $R^3$ and $R^7$; $R^4$ and $R^5$; $R^4$ and $R^6$; $R^4$ and $R^7$; $R^5$ and $R^7$ can together with the carbons to which they are attached form a cyclic structure in a similar manner as described above.

In one currently preferred embodiment, the bond between $C_9$ and $C_{10}$ is a double bond. In another currently preferred embodiment, the bond between $C_9$ and $C_{10}$ is a single bond. In another embodiment, each of $R^3$, $R^4$, $R^5$, $R^6$ and $R^7$ represents hydrogen. In yet another embodiment, the bond between $C_9$ and $C_{10}$ is a single bond, and each of $R^3$, $R^4$, $R^5$, $R^6$ and $R^7$ is hydrogen. In yet another embodiment, the bond between $C_9$ and $C_{10}$ is a double bond, and each of $R^3$, $R^4$, $R^5$, $R^6$ and $R^7$ is hydrogen.

In yet another embodiment, $R^6$ represents an oxygen atom which is bonded to $C_6$, thereby forming an oxygen-containing 5 membered heterocyclic ring. In yet another embodiment, $R^5$ represents an oxygen atom which is bonded to $C_6$, thereby forming an oxygen-containing 6 membered heterocyclic ring.

Specific examples of the compounds of formula (I) or (II) include but are not limited to:

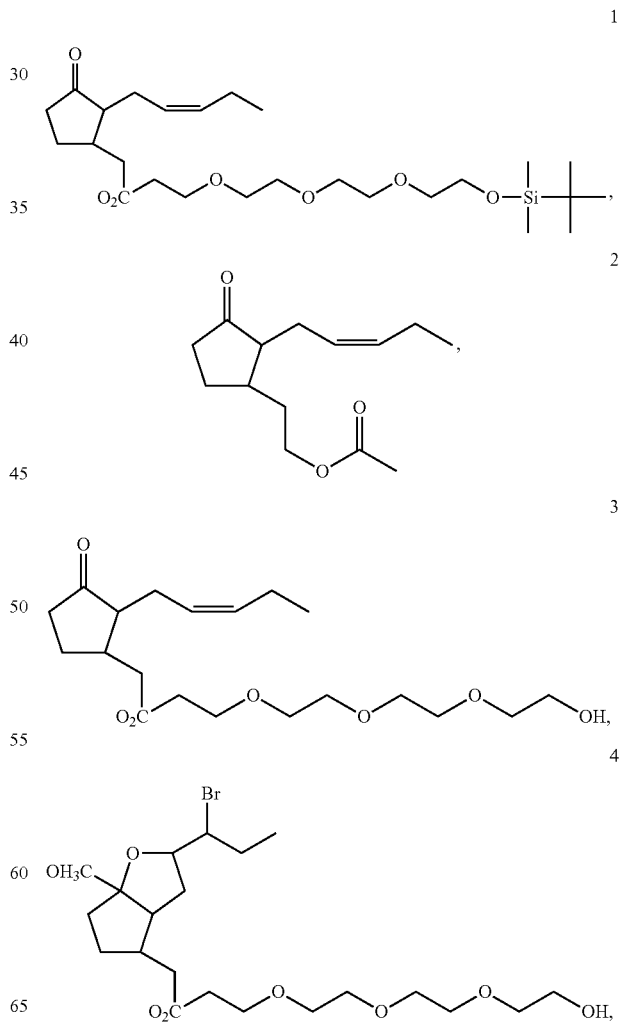

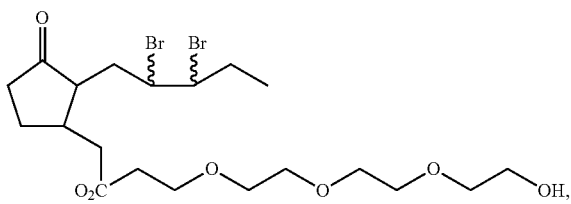

5

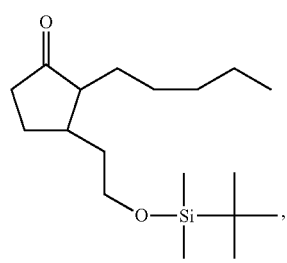

6

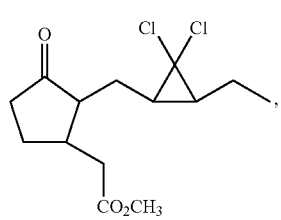

7

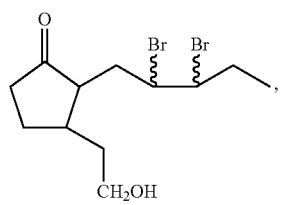

8

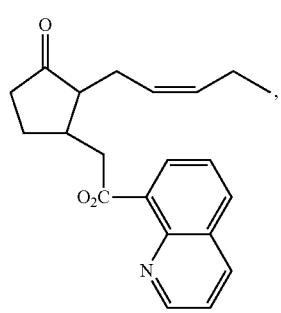

9

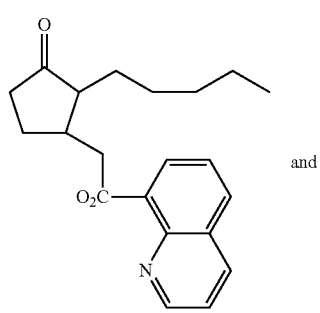

9A and

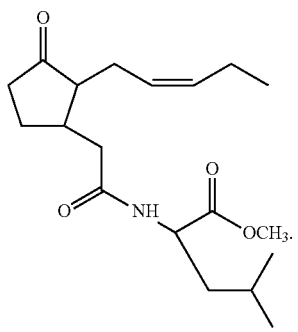

10

Additional examples of the compounds of formula II include but are not limited to:

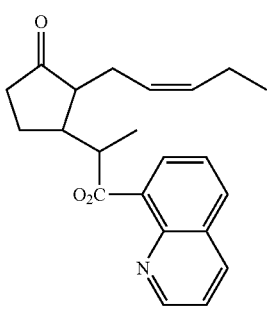

12 and

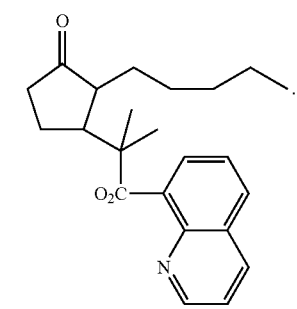

13

In yet another aspect, the present invention relates to a jasmonate derivative represented by the structure of formula II.

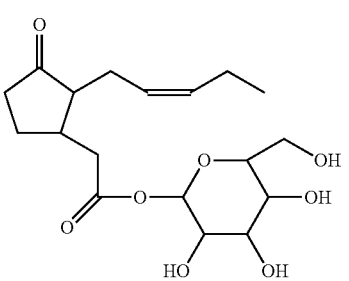

11 including salts, hydrates, solvates, polymorphs, optical isomers, geometrical isomers, enantiomers, diastereomers, and mixtures thereof. As demonstrated herein, said compound has unexpectedly been found to be a highly potent and selective cytotoxic agent, exhibiting selective cytotoxicity towards cancer cells, while having little effect on normal cells. As such, compound II possesses surprisingly superior properties as compared with the jasmonate glucosyl derivatives disclosed in U.S. Pat. No. 6,469,061.

CHEMICAL DEFINITIONS

The term "$C_1$ to $C_{12}$ alkyl" used herein alone or as part of another group denotes linear and branched, saturated groups, the latter only when the number of carbon atoms in the alkyl chain is greater than or equal to two, and can contain mixed structures. Preferred are alkyl groups containing from 1 to 4 carbon atoms ($C_1$ to $C_4$ alkyls). Examples of alkyl groups include but are not limited to methyl, ethyl, n-propyl, isopropyl, n-butyl, iso-butyl, sec-butyl, tert-butyl, amyl, tert-amyl, hexyl, heptyl, octyl, nonyl, decyl, undecyl, dodecyl and the like. Similarly, the term "$C_1$ to $C_{12}$ alkylene" denotes a bivalent radicals of 1 to 12 carbons.

The term "alkenyl" as used herein alone or as part of another group denotes an unsaturated group having at least one double bond and two or more carbon atoms. Examples of alkenyl groups include vinyl, allyl, butenyl and the like.

The term "alkynyl" as used herein alone or as part of another group denotes an unsaturated group having at least one triple bond and two or more carbon atoms. Examples of alkynyl groups include ethynyl, propynyl and the like.

Any of the $C_1$ to $C_{12}$ alkyl, the alkenyl or the alkynyl group can be unsubstituted, or substituted with one or more substituents selected from the group consisting of halogen, hydroxy, alkoxy, aryloxy, alkylaryloxy, heteroaryloxy, oxo, cycloalkyl, phenyl, heteroaryl, heterocyclyl, naphthyl, amino, alkylamino, arylamino, heteroarylamino, dialkylamino, diarylamino, alkylarylamino, alkylheteroarylamino, arylheteroarylamino, acyl, acyloxy, nitro, carboxy, carbamoyl, carboxamide, cyano, sulfonyl, sulfonylamino, sulfinyl, sulfinylamino, thiol, $C_1$ to $C_{10}$ alkylthio arylthio, or $C_1$ to $C_{10}$ alkylsulfonyl groups. Any substituent can be unsubstituted or further substituted with any one of these aforementioned substituents.

The term "$C_3$ to $C_8$ cycloalkyl" used herein alone or as part of another group denotes any saturated or unsaturated (e.g., cycloalkenyl, cycloalkynyl) monocyclic or polycyclic group. Nonlimiting examples of cycloalkyl groups are cyclopropyl, cyclobutyl, cyclopentyl, cyclohexyl or cycloheptyl. Examples or cycloalkenyl groups include cyclopentenyl, cyclohexenyl and the like. The cycloalkyl group can be unsubstituted or substituted with any one or more of the substituents defined above for alkyl. Similarly, the term "cycloalkylene" means a bivalent cycloalkyl, as defined above, where the cycloalkyl radical is bonded at two positions connecting together two separate additional groups.

The term "aryl" used herein alone or as part of another group denotes an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. The aryl group can be unsubstituted or substituted through available carbon atoms with one or more groups defined hereinabove for alkyl.

The term "heteroaryl" used herein alone or as part of another group denotes a heteroaromatic system containing at least one heteroatom ring atom selected from nitrogen, sulfur and oxygen. The heteroaryl contains 5 or more ring atoms. The heteroaryl group can be monocyclic, bicyclic, tricyclic and the like. Also included in this expression are the benzo-heterocyclic rings. If nitrogen is a ring atom, the present invention also contemplates the N-oxides of the nitrogen containing heteroaryls. Nonlimiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, quinolyl (e.g. 1-quinolinyl, 2-quinolinyl, 3-quinolinyl, 4-quinolinyl, 5-quinolinyl, 6-quinolinyl, 7-quinolinyl and 8-quinolinyl), isoquinolinyl (e.g., 1-isoquinolinyl, 2-isoquinolinyl, 3-isoquinolinyl, 4-isoquinolinyl, 5-isoquinolinyl, 6-isoquinolinyl, 7-isoquinolinyl and 8-isoquinolinyl); naphthyridinyl (e.g., 1-naphthyridinyl, 2-naphthyridinyl), quinoxalinyl, quinazolinyl, cinnolinyl, pteridinyl, carbolinyl, thiazolyl, oxazolyl, isothiazolyl, isoxazolyl and the like. The heteroaryl group can optionally be substituted through available atoms with one or more groups defined hereinabove for alkyl. The heteroaryl group can be unsubstituted or substituted through available atoms with one or more groups defined hereinabove for alkyl.

The term "heterocyclic ring" or "heterocyclyl" used herein alone or as part of another group denotes a five-membered to eight-membered rings that have 1 to 4 heteroatoms, such as oxygen, sulfur and/or nitrogen, in particular nitrogen, either alone or in conjunction with sulfur or oxygen ring atoms. These five-membered to eight-membered rings can be saturated, fully unsaturated or partially unsaturated, with fully saturated rings being preferred. Preferred heterocyclic rings include piperidinyl, piperidinyl, pyrrolidinyl pyrrolinyl, pyrazolinyl, pyrazolidinyl, piperidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, and the like. The heterocyclyl group can be unsubstituted or substituted through available atoms with one or more groups defined hereinabove for alkyl.

The term "halogen" or "halo" as used herein alone or as part of another group refers to chlorine, bromine, fluorine, and iodine.

The term "amino" as used herein alone or as part of another group refers to an $NH_2$ group. The terms "alkyl amino, dialkylamino, arylamino, diaryl amino, heteroarylamino, diheteroarylamino" and variants thereof as used herein refer to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl and the like. These substituents can be further substituted with any one or more of the substituents defined above for alkyl. In addition, the amino substituents (e.g., $NR^{9a}R^{9b}$) can together with the nitrogen atom to which they are attached form a heterocyclic ring which can be any one of the heterocyclic rings defined above.

The term "hydroxy" refers to an OH group. The terms "alkoxy", "aryloxy" "arylalkyloxy" or "heteroaryloxy" as used herein alone or as part of another group includes any of the above alkyl, aryl or heteroaryl groups linked to an oxygen atom. Nonlimiting examples of an alkoxy group is methoxy, ethoxy, n-propoxy, isopropoxy, n-butoxy, t-butoxy and like groups. An example of an aryloxy group is phenyloxy (phenoxy). The alkoxy, aryloxy, arylalkyloxy or heteroaryloxy groups can be unsubstituted or substituted with any one or more of the substituents defined above for alkyl.

The term "hydroxy protecting group" as used herein refers to a readily cleavable groups) bonded to hydroxyl groups. The nature of the hydroxy-protecting groups is not critical so long as the derivatized hydroxyl group is stable. An example of a hydroxy protecting group is a silyl group, which can be substituted with alkyl (trialkylsilyl), with an aryl (triarylsilyl) or a combination thereof (e.g., dialkylphenylsilyl). A preferred example of a silyl protecting group is trimethylsilyl (TMS) or di-t-butyldimethyl silyl (TBDMS). Other examples of hydroxy protecting groups include, for example, $C_1$-$C_4$ alkyl, —CO—($C_1$-$C_6$ alkyl), —SO$_2$—($C_1$-$C_6$ alkyl), —SO$_2$-aryl, —CO—Ar in which Ar is an aryl group as defined above, and —CO—($C_1$-$C_6$ alkyl)Ar (e.g., a carboxybenzyl group). Other examples of hydroxy-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in OrganicSynthesis, "2nd ed., John Wiley and Sons, New York, N.Y., 1991, Chapters 2 and 3, each of which is incorporated herein by reference.

The term "carboxy" as used herein alone or as part of another group refers to a COO group, and further encompasses carboxylate salts thereof of the formula COOM wherein M is a metal ion. The term "metal ion" refers to alkali metal ions such as sodium, potassium or lithium and alkaline earth metal ions such as magnesium and calcium, as well as zinc and aluminum.

The term "carboxy-protecting group" as used herein refers to one of the derivatives of the carboxylic acid group commonly employed to block or protect the carboxylic acid groups. A non-limiting of a carboxyl protecting group is a $C_1$-$C_{12}$ alkyl group which, together with the carboxy group, define an ester, e.g., methyl ester. Another example of a carboxy protecting group is a benzyl group. Other examples of these groups are found in E. Haslam, "Protective Groups in Organic Chemistry," J. G. W. McOmie, Ed., Plenum Press, New York, N.Y., 1973, Chapter 5, and T. W. Greene and P. G. M. Wuts, "Protective Groups in Organic Synthesis," 2nd ed., John Wiley and Sons, New York, N.Y., 1991, Chapter 5, each of which is incorporated herein by reference.

The term "acyl" encompasses groups such as formyl, acetyl, propionyl, butyryl, pentanoyl, pivaloyl, hexanoyl, heptanoyl, octanoyl, nonanoyl, decanoyl, undecanoyl, dodecanoyl, benzoyl and the like. Preferred acyl groups are acetyl and benzoyl.

The term "thio" as used herein alone or as part of another group refers to an SH group. The terms "alkylthio", "arylthio" or "arylalkylthio" as used herein alone or as part of another group refer to any of the above alkyl, arylalkyl or aryl groups linked to a sulfur atom.

The term "sulfonyl" as used herein alone or as part of another group refers to —S(O)$_2$—. The term "sulfonylamino" as used herein alone or as part of another group refers to —S(O)$_2$—NH. The term "sulfinyl" refers to —S(O)—. The term "sulfinylamino" as used herein alone or as part of another group refers to —S(O)—NH. The term "oxo" as used herein alone or as part of another group refers to —O—. The term "cyano" as used herein alone or as part of another group refers to a CN group. The term "nitro" as used herein alone or as part of another group refers to an NO$_2$ group.

The term "polyoxyalkylene" e.g., "polyoxy $C_1$-$C_{12}$ alkylene" as used herein alone or as part of another group refers to two or more units of oxyalkylene (e.g., a $C_1$-$C_{12}$ alkylene moiety as defined above bonded to an oxygen), for example a compound represented by the structure —O[(CH$_2$)$_p$O)]$_m$— wherein m is an integer of 1 to 20 and p is an integer of 1 to 12. An example of a polyoxy $C_1$-$C_{12}$ alkylene group is polyethylene glycol represented by the structure —O(CH$_2$—CH$_2$—O)$_m$—, for example —O(CH$_2$—CF$_{12}$—O)$_4$—.

Similarly, the term "polyaminoalkylene", e.g., "polyamino $C_1$-$C_{12}$ alkylene" as used herein alone or as part of another group refers to two or more units of aminoalkyene (e.g., a $C_1$-$C_{12}$ alkylene moiety as defined above bonded to an NH), for example a compound represented by the structure —NH[(CH$_2$)$_p$NH)]$_m$— wherein m is an integer of 1 to 20 and p is an integer of 1 to 12. An example of a polyamino $C_1$-$C_{12}$ alkylene group is polyethylenediamine represented by the structure —NH(CH$_2$—CH$_2$—NH)$_m$.

Similarly, the term "polythioalkylene", e.g., "polythio $C_1$-$C_{12}$ alkylene" as used herein alone or as part of another group refers to two or more units of thioalkylene (e.g., a $C_1$-$C_{12}$ alkylene moiety as defined above bonded to a sulfur), for example a compound represented by the structure —S[(CH$_2$)$_p$S)]$_m$— wherein m is an integer of 1 to 20 and p is an integer of 1 to 12. An example of a polythio $C_1$-$C_{12}$ alkylene group is represented by the structure —S(CH$_2$—CH$_2$—S)$_m$.

The terms "natural and unnatural amino acids" ($\alpha$-amino acid) refers to both the naturally occurring amino acids and other unnaturally amino acids including both optically active (D and L) forms as well as racemic derivatives. As contemplated herein, the amino acids are conjugated to the jasmonate derivatives by forming an amide bond between the carboxyl group of the jasmonate and the amino group of the amino acid. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, $\gamma$-carboxyglutamic acid, arginine, ornithine and lysine. Examples of unnatural $\alpha$-amino acids include N-methyl-alanine, $\alpha$-aminoisobutyric acid, $\alpha$-aminobutyric acid, $\gamma$-aminobutyric acid, citrulline, N-methyl-glycine, N-methyl-glutamic acid, homocitrulline, homoproline, homoserine, hydroxyproline, norleucine, 4-aminophenylalanine, statine, hydroxylysine, kynurenine, 3-(2'-naphthyl)alanine, 3-(1'-naphthyl)alanine, methionine sulfone, (t-butyl)alanine, (t-butyl)glycine, 4-hydroxyphenylglycine, aminoalanine, phenylglycine, vinylalanine, propargyl-gylcine, 1,2,4-triazolo-3-alanine, thyronine, 6-hydroxytryptophan, 5-hydroxytryptophan, 3-hydroxykynurenine, 3-aminotyrosine, trifluoromethyl-alanine, 2-thienylalanine, (2-(4-pyridyl)ethyl)cysteine, 3,4-dimethoxy-phenylalanine, 3-(2'-thiazolyl)alanine, ibotenic acid, 1-amino-1-cyclopentanecarboxylic acid, 1-amino-1-cyclohexanecarboxylic acid, quisqualic acid, 3-(trifluoromethylphenyl)alanine, (cyclohexyl)glycine, thiohistidine, 3-methoxytyrosine, elastatinal, norleucine, norvaline, alloisoleucine, homoarginine, thioproline, dehydroproline, hydroxyproline, homoproline, $\alpha$-amino-n-butyric acid, cyclohexylalanine, 2-amino-3-phenylbutyric acid, $\beta$-2- and 3-thienylalanine, $\beta$-2- and 3-furanylalanine, $\beta$-2-, 3- and 4-pyridylalanine, 13-(benzothienyl-2- and 3-yl)alanine, $\beta$-(1- and 2-naphthyl)alanine, O-alkylated derivatives of serine, threonine or tyrosine, S-alkylated cysteine, S-alkylated homocysteine, O-sulfate, O-phosphate and O-carboxylate esters of tyrosine, 3-(sulfo)tyrosine, 3-(carboxy)tyrosine, 3-(phospho)tyrosine, the 4-methane sulfonic acid ester of tyrosine, 4-methane phosphonic acid ester of tyrosine, 3,5-diiodotyrosine, 3-nitrotyrosine, $\epsilon$-alkyl lysine, and $\delta$-alkyl ornithine.

All stereoisomers of the compounds of the instant invention are contemplated, either in admixture or in pure or substantially pure form. The compounds of the present invention can have asymmetric centers at any of the atoms. Consequently, the compounds can exist in enantiomeric or diastereomeric forms or in mixtures thereof. The present invention contemplates the use of any racemates (i.e. mixtures containing equal amounts of each enantiomers), enantiomerically enriched mixtures (i.e., mixtures enriched for one enantiomer), pure enantiomers or diastereomers, or any mixtures thereof. The chiral centers can be designated as R or S or R,S or d,D, l,L or d,l, D,L. Compounds comprising amino acid residues include residues of D-amino acids, L-amino acids, or racemic derivatives of amino acids. Compounds comprising sugar residues include residues of D-sugars, L-sugars, or racemic derivatives of sugars. In addition, several of the compounds of the invention contain one or more double bonds. The present invention intends to encompass all structural and geometrical isomers including cis, trans, E and Z isomers.

One or more of the compounds of the invention, may be present as a salt. The term "salt" encompasses both basic and acid addition salts, including but not limited to carboxylate salts or salts with amine nitrogens, and include salts formed with the organic and inorganic anions and cations discussed below. Furthermore, the term includes salts that form by standard acid-base reactions with basic groups (such as amino groups) and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, cinnamic, and like acids.

The term "organic or inorganic cation" refers to counter-ions for the carboxylate anion of a carboxylate salt. The counter-ions are chosen from the alkali and alkaline earth metals, (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl) ammonium, phenylethylbenzylammonium, dibenzylethylenediammonium, and like cations. See, for example, "Pharmaceutical Salts," Berge et al., J. Pharm. Sci., 66:1-19 (1977), which is incorporated herein by reference. Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amino group are also contemplated.

The present invention also includes solvates of the compounds of the present invention and salts thereof. "Solvate" means a physical association of a compound of the invention with one or more solvent molecules. This physical association involves varying degrees of ionic and covalent bonding, including hydrogen bonding. In certain instances the solvate will be capable of isolation. "Solvate" encompasses both solution-phase and isolatable solvates. Non-limiting examples of suitable solvates include ethanolates, methanolates and the like. "Hydrate" is a solvate wherein the solvent molecule is water.

The present invention also includes polymorphs of the compounds of the present invention and salts thereof. The term "polymorph" refers to a particular crystalline state of a substance, which can be characterized by particular physical properties such as X-ray diffraction, IR spectra, melting point, and the like.

Therapeutic Use

As described herein, the compounds of the present invention are potent cytotoxic agents that are capable of inhibiting cancer cell proliferation in a wide variety of cancer cells. The present invention thus provides powerful methods to the chemoprevention and treatment of cancer that have not been previously described.

Thus, in one aspect the present invention additionally provides a method for inhibiting cancer cell proliferation, comprising contacting the cancer cells with a therapeutically effective amount of a compound of the present invention, as described herein. Preferably, the compound is one or more of the compounds represented by any of formulas I, II, 1, 2, 3, 4, 5, 6, 7, 8, 9, 9A, 10, 11, 12 or 13 as described herein. In some embodiments, the compound is administered in a pharmaceutical composition.

Furthermore, the present invention provides a method for the treatment of cancer in a subject, by administering to the subject a therapeutically effective amount of the compound of the invention, as described herein. Preferably, the compound is one or more of the compounds represented by any of formulas I, II, 1, 2, 3, 4, 5, 6, 7, 8, 9, 9A, 10, 11, 12 or 13 as described herein. In some embodiments, the compound is administered in a pharmaceutical composition. In one embodiment, the subject is a mammal, preferably a human. However, the present invention also contemplates using the compounds of the present invention for non-human mammals, e.g., in veterinary medicine.

Furthermore, the present invention relates to the use of a compound of any of formulas I, II 1, 2, 3, 4, 5, 6, 7, 8, 9, 9A, 10, 11, 12 or 13 according to the present invention in the preparation of a medicament useful for the treatment of cancer.

It is to be understood that whenever the terms "treating or inhibiting a malignant cell proliferative disease or disorder", "treating or inhibiting a non-solid cancer", "treating or inhibiting a tumor" are used herein in the description and in the claims, they are intended to encompass tumor formation, primary tumors, tumor progression or tumor metastasis.

The term "inhibition of proliferation" in relation to cancer cells, in the context of the present invention refers to a decrease in at least one of the following: number of cells (due to cell death which may be necrotic, apoptotic or any other type of cell death or combinations thereof) as compared to control; decrease in growth rates of cells, i.e. the total number of cells may increase but at a lower level or at a lower rate than the increase in control; decrease in the invasiveness of cells (as determined for example by soft agar assay) as compared to control even if their total number has not changed; progression from a less differentiated cell type to a more differentiated cell type; a deceleration in the neoplastic transformation; or alternatively the slowing of the progression of the cancer cells from one stage to the next.

The term "treatment of cancer" in the context of the present invention includes at least one of the following: a decrease in the rate of growth of the cancer (i.e. the cancer still grows but at a slower rate); cessation of growth of the cancerous growth, i.e., stasis of the tumor growth, and, in preferred cases, the tumor diminishes or is reduced in size. The term also includes reduction in the number of metastasis, reduction in the number of new metastasis formed, slowing of the progression of cancer from one stage to the other and a decrease in the angiogenesis induced by the cancer. In most preferred cases, the tumor is totally eliminated. Additionally included in this term is lengthening of the survival period of the subject undergoing treatment, lengthening the time of diseases progression, tumor regression, and the like. This term also encompasses prevention for prophylactic situations or for those individuals who are susceptible to contracting a tumor. The administration of the compounds of the present invention will reduce the likelihood of the individual contracting the disease. In preferred situations, the individual to whom the compound is administered does not contract the disease.

As used herein, the term "administering" refers to bringing in contact with a compound of the present invention. Administration can be accomplished to cells or tissue cultures, or to living organisms, for example humans. In one embodiment, the present invention encompasses administering the compounds of the present invention to a human subject.

A "therapeutic" treatment is a treatment administered to a subject who exhibits signs of pathology for the purpose of diminishing or eliminating those signs. A "therapeutically effective amount" of a compound of the invention is that amount of compound which is sufficient to provide a beneficial effect to the subject to which the compound is administered.

The term "cancer" in the context of the present invention includes all types of neoplasm whether in the form of solid or non-solid tumors, and includes both malignant and premalignant conditions as well as their metastasis.

Cancers may be classified in two ways: by the type of tissue in which the cancer originates (histological type) and by primary site, or the location in the body where the cancer first developed. The international standard for the classification and nomenclature of histologies is the International Classification of Diseases for Oncology, Third Edition.

From a histological standpoint there are hundreds of different cancers, which are grouped into five major categories: carcinoma, sarcoma, myeloma, leukemia, and lymphoma. In addition, there are also some cancers of mixed types.

Carcinoma refers to a malignant neoplasm of epithelial origin or cancer of the internal or external lining of the body. Carcinomas, malignancies of epithelial tissue, account for 80 to 90 percent of all cancer cases. Epithelial tissue is found throughout the body. It is present in the skin, as well as the covering and lining of organs and internal passageways, such as the gastrointestinal tract.

Carcinomas are divided into two major subtypes: adenocarcinoma, which develops in an organ or gland, and squamous cell carcinoma, which originates in the squamous epithelium. Most carcinomas affect organs or glands capable of secretion, such as the breasts, which produce milk, or the lungs, which secrete mucus, or colon or prostate or bladder.

Adenocarcinomas generally occur in mucus membranes and are first seen as a thickened plaque-like white mucosa. They often spread easily through the soft tissue where they occur. Squamous cell carcinomas occur in many areas of the body.

Sarcoma refers to cancer that originates in supportive and connective tissues such as bones, tendons, cartilage, muscle, and fat. Generally occurring in young adults, the most common sarcoma often develops as a painful mass on the bone. Sarcoma tumors usually resemble the tissue in which they grow.

Examples of sarcomas are: Osteosarcoma or osteogenic sarcoma (bone); Chondrosarcoma (cartilage); Leiomyosarcoma (smooth muscle); Rhabdomyosarcoma (skeletal muscle); Mesothelial sarcoma or mesothelioma (membranous lining of body cavities); Fibrosarcoma (fibrous tissue); Angiosarcoma or hemangioendothelioma (blood vessels); Liposarcoma (adipose tissue); Glioma or astrocytoma (neurogenic connective tissue found in the brain); Myxosarcoma (primitive embryonic connective tissue); Mesenchymous or mixed mesodermal tumor (mixed connective tissue types);

Myeloma is cancer that originates in the plasma cells of bone marrow. The plasma cells produce some of the proteins found in blood.

Leukemias ("non-solid tumors" or "blood cancers") are cancers of the bone marrow (the site of blood cell production). The disease is often associated with the overproduction of immature white blood cells. Leukemia also affects red blood cells and can cause poor blood clotting and fatigue due to anemia. Examples of leukemia include: Myelogenous or granulocytic leukemia (malignancy of the myeloid and granulocytic white blood cell series); Lymphatic, lymphocytic, or lymphoblastic leukemia (malignancy of the lymphoid and lymphocytic blood cell series); Polycythemia vera or erythremia (malignancy of various blood cell products, but with red cells predominating)

Lymphomas develop in the glands or nodes of the lymphatic system, a network of vessels, nodes, and organs (specifically the spleen, tonsils, and thymus) that purify bodily fluids and produce infection-fighting white blood cells, or lymphocytes. Unlike the leukemias, which are sometimes called "non-solid tumors," lymphomas are "solid cancers." Lymphomas may also occur in specific organs such as the stomach, breast or brain. These lymphomas are referred to as extranodal lymphomas. The lymphomas are subclassified into two categories: Hodgkin lymphoma and Non-Hodgkin lymphoma. The presence of Reed-Sternberg cells in Hodgkin lymphoma diagnostically distinguishes Hodgkin lymphoma from Non-Hodgkin lymphoma.

Mixed Type cancers contain several types of cells. The type components may be within one category or from different categories. Some examples are: adenosquamous carcinoma; mixed mesodermal tumor; carcinosarcoma; teratocarcinoma As used herein, the term "cancer" includes the above categories of carcinoma, sarcoma, myeloma, leukemia, lymphoma and mixed type tumors. In particular, the term cancer includes: lymphoproliferative disorders, breast cancer, ovarian cancer, prostate cancer, cervical cancer, endometrial cancer, bone cancer, liver cancer, stomach cancer, colon cancer, pancreatic cancer, cancer of the thyroid, head and neck cancer, cancer of the central nervous system, cancer of the peripheral nervous system, skin cancer, kidney cancer, as well as metastases of all the above. More particularly, as used herein the term may refer to: hepatocellular carcinoma, hematoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, melanoma, squamous cell carcinoma, basal cell carcinoma, adenocarcinoma (well differentiated, moderately differentiated, poorly differentiated or undifferentiated), renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, astrocyoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma.

More preferably, the cancer is selected from the group consisting of prostate cancer, breast cancer, skin cancer, colon cancer, lung cancer, pancreatic cancer, lymphoma, myeloma, leukemia, head and neck cancer, kidney cancer, stomach cancer, ovarian cancer, bone cancer, liver cancer or thyroid cancer. Even more preferably, the cancer is selected from leukemia, including lymphoblastic leukemia, lung carcinoma, melanoma, kidney cancer, stomach cancer and colon cancer.

In other embodiments of the use of preparing a medicament, the medicament additionally comprises at least one active chemotherapeutic agent other than the compounds of the invention. In certain embodiments, the compounds of the invention may be administered alongside with at least one traditional chemotherapeutic drug that is effective at treating the particular cancer. The administration can be concurrent (either combined in one dosage form or in separate dosage forms) or sequential. If provided sequentially, the jasmonate derivative can be administered before or after treatment with the additional chemotherapeutic agent(s). The combination of a compound of the invention and the traditional drug may allow administration of a lower dosage of the traditional drug, and thus the side effects experienced by the subject may be significantly lower, while a sufficient chemotherapeutic effect is nevertheless achieved.

Pharmaceutical Compositions

Although the heterocyclic jasmonate derivatives of the present invention can be administered alone, it is contemplated that these compounds will be administered in a pharmaceutical composition containing the jasmonate derivative together with a pharmaceutically acceptable carrier or excipient.

Preferably, in the pharmaceutical composition the active ingredient is dissolved in any acceptable lipid carrier (e.g., fatty acids, oils to form, for example, a micelle or a liposome). Further, in accordance with a preferred embodiment of the present invention, the composition additionally comprises at least one other chemotherapeutic agent The pharmaceutical compositions of the present invention can be formulated for administration by a variety of routes including oral, rectal, transdermal, parenteral (subcutaneous, intraperitoneal, intravenous, intraarterial, transdermal and intramuscular), topical, intranasal, or via a suppository. Such compositions are prepared in a manner well known in the pharmaceutical art and comprise as an active ingredient at least one compound of the present invention as described hereinabove, and a pharmaceutically acceptable excipient or a carrier. The term "pharmaceutically acceptable" means approved by a regulatory agency of the Federal or a state government or listed in the U.S. Pharmacopeia or other generally recognized pharmacopeia for use in animals and, more particularly, in humans.

During the preparation of the pharmaceutical compositions according to the present invention the active ingredient is usually mixed with a carrier or excipient, which may be a solid, semi-solid, or liquid material. The compositions can be in the form of tablets, pills, capsules, pellets, granules, powders, lozenges, sachets, cachets, elixirs, suspensions, dispersions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

The carriers may be any of those conventionally used and are limited only by chemical-physical considerations, such as solubility and lack of reactivity with the compound of the invention, and by the route of administration. The choice of carrier will be determined by the particular method used to administer the pharmaceutical composition. Some examples of suitable carriers include lactose, glucose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water and methylcellulose. The formulations can additionally include lubricating agents such as talc, magnesium stearate, and mineral oil; wetting agents, surfactants, emulsifying and suspending agents; preserving agents such as methyl- and propylhydroxybenzoates; sweetening agents; flavoring agents, colorants, buffering agents (e.g., acetates, citrates or phosphates), disintegrating agents, moistening agents, antibacterial agents, antioxidants (e.g., ascorbic acid or sodium bisulfite), chelating agents (e.g., ethylenediaminetetraacetic acid), and agents for the adjustment of tonicity such as sodium chloride. Other pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

Any method can be used to prepare the pharmaceutical compositions. Solid dosage forms can be prepared by wet granulation, dry granulation, direct compression and the like.

The solid dosage forms of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compositions of the present invention may be incorporated, for administration orally or by injection, include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insulation include solutions and suspensions in pharmaceutically acceptable aqueous or organic solvents, or mixtures thereof, and powders. The liquid or solid compositions may contain suitable pharmaceutically acceptable excipients as described above. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices that deliver the formulation in an appropriate manner.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art.

In yet another embodiment, the composition is prepared for topical administration, e.g. as an ointment, a gel a drop or a cream. For topical administration to body surfaces using, for example, creams, gels, drops, ointments and the like, the compounds of the present invention can be prepared and applied in a physiologically acceptable diluent with or without a pharmaceutical carrier. The present invention may be used topically or transdermally to treat cancer, for example, melanoma. Adjuvants for topical or gel base forms may include, for example, sodium carboxymethylcellulose, polyacrylates, polyoxyethylene-polyoxypropylene-block polymers, polyethylene glycol and wood wax alcohols.

Alternative formulations include nasal sprays, liposomal formulations, slow-release formulations, controlled-release formulations and the like, as are known in the art.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In preparing a formulation, it may be necessary to mill the active ingredient to provide the appropriate particle size prior to combining with the other ingredients. If the active compound is substantially insoluble, it ordinarily is milled to a particle size of less than 200 mesh. If the active ingredient is substantially water soluble, the particle size is normally adjusted by milling to provide a substantially uniform distribution in the formulation, e.g. about 40 mesh.

It may be desirable to administer the pharmaceutical composition of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material. According to some preferred embodiments, administration can be by direct injection e.g., via a syringe, at the site of a tumor or neoplastic or pre-neoplastic tissue.

The compounds may also be administered by any convenient route, for example by infusion or bolus injection, by absorption through epithelial linings (e.g., oral mucosa, rectal and intestinal mucosa, etc.), and may be administered together with other therapeutically active agents. It is preferred that administration is localized, but it may be systemic. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir. Pulmonary administration can also be employed, e.g., by use of an inhaler or nebulizer, and formulation with an aerosolizing agent.

A compound of the present invention can be delivered in an immediate release or in a controlled release system. In one embodiment, an infusion pump may be used to administer a compound of the invention, such as one that is used for delivering chemotherapy to specific organs or tumors (see Buchwald et al., 1980, Surgery 88: 507; Saudek et al., 1989, N. Engl. J. Med. 321: 574). In a preferred form, a compound of the invention is administered in combination with a biodegradable, biocompatible polymeric implant, which releases the compound over a controlled period of time at a selected site. Examples of preferred polymeric materials include polyanhydrides, polyorthoesters, polyglycolic acid, polylactic acid, polyethylene vinyl acetate, copolymers and blends thereof (See, Medical applications of controlled release, Langer and Wise (eds.), 1974, CRC Pres., Boca Raton, Fla.). In yet another embodiment, a controlled release system can be placed in proximity of the therapeutic target, thus requiring only a fraction of the systemic dose.

Furthermore, at times, the pharmaceutical compositions may be formulated for parenteral administration (subcutaneous, intravenous, intraarterial, transdermal, intraperitoneal or intramuscular injection) and may include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives. Oils such as petroleum, animal, vegetable, or synthetic oils and soaps such as fatty alkali metal, ammonium, and triethanolamine salts, and suitable detergents may also be used for parenteral administration. The above formulations may also be used for direct intra-tumoral injection. Further, in order to minimize or eliminate irritation at the site of injection, the compositions may contain one or more nonionic surfactants. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described and known in the art.

Alternatively, the jasmonate derivatives of the present invention can be used in hemodialysis such as leukophoresis and other related methods, e.g., blood is drawn from the patient by a variety of methods such dialysis through a column/hollow fiber membrane, cartridge etc, is treated with the jasmonate derivatives Ex-vivo, and returned to the patient following treatment. Such treatment methods are well known and described in the art. See, e.g., Kolho et al. (J. Med. Virol. 1993, 40(4): 318-21); Ting et al. (Transplantation, 1978, 25(1): 31-3); the contents of which are hereby incorporated by reference in their entirety.

The amount of a compound of the invention that will be effective in the treatment of a particular disorder or condition, including cancer, will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. A preferred dosage will be within the range of 0.01-1000 mg/kg of body weight, more preferably, 0.1 mg/kg to 100 mg/kg and even more preferably 1 mg/kg to 10 mg/kg. Effective doses may be extrapolated from dose-response curves derived from in vitro or animal model test bioassays or systems.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

cells in 100 µl per well) seeded in 96-well plates. Adherent cells (CT26 and MCF7) were allowed to adhere over-night.

Jasmonate-derivatives were added at concentration ranging from 0.005-0.5 mM for 24 hours. Each experimental point was performed in triplicates. Untreated cells were used as control. The jasmonate-derivatives were prepared as a stock of 167 mM in 100% ethanol. Dilutions were performed in culture medium and ethanol so that the final concentration of ethanol in each well was 0.6%. This concentration of ethanol by itself did not affect the viability of any of the cell lines.

Optical density representing viable cells was determined using the XTT Cell Proliferation Kit assay (Biological industries, Beit-Haemek, Israel).

Percentage of Optical density is directly proportional to the number of living cells in culture. Cytotoxicity (%) was calculated in the following way: [(OD of control cells−OD of drug-treated cells)/OD of control cells]×100.

Results

IC 50 values for the different compounds in different cell lines are listed in Table 1 below.

TABLE 1

| Compound | IC50 in Molt-4 (mM) | IC50 in CT-26 (mM) | IC50 in MCF-7 (mM) | IC50 in PBL | Remarks |
|---|---|---|---|---|---|
| 1 | 0.210 ± 0.111 | 0.307 ± 0.167 | 0.220 ± 0.000 | >0.500 | |
| 2 | 0.440 ± 0.109 | >0.500 | >0.500 | >0.500 | |
| 3 | 0.340 ± 0.226 | 0.340 ± 0.226 | >0.500 | Not done | |
| 4 | 0.037 ± 0.038 | 0.135 ± 0.049 | 0.070 ± 0.000 | 0.060 ± 0.014 | |
| 5 | 0.086 ± 0.058 | 0.430 ± 0.099 | >0.500 | 0.220 ± 0.000 | |
| 6 | 0.056 ± 0.011 | 0.263 ± 0.212 | 0.236 ± 0.180 | 0.090 ± 0.014 | |
| 7 | 0.125 ± 0.026 | 0.393 ± 0.141 | 0.323 ± 0.075 | 0.425 ± 0.021 | |
| 8 | 0.050 ± 0.028 | 0.163 ± 0.042 | 0.120 ± 0.060 | 0.06 ± 0.014 | |
| 9 | 0.012 ± 0.009 | 0.029 ± 0.021 | 0.060 ± 0.014 | 0.200 ± 0.085 | |
| 9A | 0.01 | | | | |
| 10 | 0.243 ± 0.039 | >0.5 | — | >0.5 | |
| 11 | 0.079 ± 0.006 | 0.237 ± 0.029 | 0.110 ± 0.020 | 0.323 ± 0.211 | |
| 12 | 0.025 | | | | |
| 13 | 0.009 | | | | |

EXAMPLES

Example 1

Cytotoxicity of Jasmonate Derivatives Towards Leukemia Cells

New jasmonate-derivatives (compounds 1-11) were tested for cytotoxicity in 3 cancer cell lines:
A) Molt-4—Human acute lymphoblastic leukemia cell-line
B) CT26—Murine colon carcinoma cell-line
C) MCF7—Human breast adenocarcinoma cell-line The new derivatives were also tested on normal lymphocytes (PBL) obtained from healthy donors and stimulated with Phytohemagglutinine (PHA) and TPA. The experimental set up as well as IC50 values obtained for the different cell lines are listed below.

Experimental Set Up:

Mononuclear cells were isolated from peripheral blood of healthy donors by ficoll-hypaque density gradient centrifugation. The mononuclear cells were allowed to adhere to plastic dishes to remove macrophages. The non-adherent peripheral blood lymphocytes (PBL) were pre-incubated with 0.8 µg/mL PHA and 5 ng/mL TPA for 24 hours and then used in further experiments.

Cell densities were as follows: Molt-4 (at $2.5 \times 10^4$ cells in 100 µl per well), CT26 (at $5 \times 10^3$ cells in 100 µl, per well), MCF7 (at $5 \times 10^3$ cells in 100 µL per well) and PBL (at $1.5 \times 10^5$ Example 2

Selectivity of Jasmonate Derivatives: Compounds 9 and 11

Experimental Set Up

Mononuclear cells were isolated from peripheral blood of healthy donors and treated as described above. The non-adherent PBL were pre-incubated with PHA and TPA as described above. Molt-4 and PBL cells were seeded in 96-well plates as described above.

Jasmonate derivatives, compound 9 and compound II, were added at concentration ranging from 0.005-0.5 mM for 24 hours. Each experimental point was performed in triplicates. Untreated cells were used as control. The Jasmonate-derivatives were prepared as a stock of 167 mM in 100% ethanol and dilutions in medium were prepared as described above. Optical density and percentage of Cytotoxicity were determined as described above.

Figure 1B:
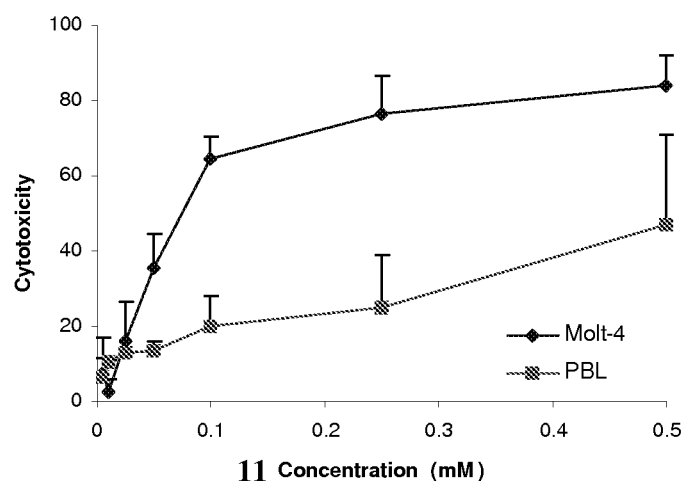

As shown in FIGS. 1A and 1B, there is a comfortable therapeutic window which allows compounds 9 and 11 to kill leukemic cells without exerting a substantial effect on normal lymphocytes. The results demonstrate the ability of the compounds of the present invention to exert a selective cytotoxic effect against cancer cells, without substantially affecting normal cells.

Example 3

Effect of Compound 9 Tested In Vitro in a Clonogenic Assay (TCA) in Different Patients' Derived Tumors Experimental Set Up Cancer cells were taken directly from cancer patients, employing the Tumor-Colony-Assay: Solid human tumor xenografts growing subcutaneously in serial passages in thymus aplastic nude mice were removed and disaggregated to obtain isolated tumor cells. Viable cells were added to culture medium supplemented with agar and plated in 24-multiwell dishes. The test compound was applied in the cultures that were incubated at 37° C. for 6-20 days and monitored for colony growth using an inverted microscope. At the time of maximum colony formation, colonies were counted and 24 hours prior to evaluation, stained with a vital dye. Drug effects were expressed in terms of the percentage of colony formation, obtained by comparison of the mean number of colonies in the treated wells with the mean colony count of untreated controls. $IC_{50}$ values, being the drug concentrations necessary to inhibit colony formation by 50%, were determined by plotting compound concentration versus relative colony count. Results are depicted in Table 2.

TABLE 2

Effect of Compound 9 tested in vitro in a clonogenic assay (TCA) in different patients' derived tumors

| Tissue origin | Tumor model | Histology | IC50 (µM) |
|---|---|---|---|
| Colon | CXF 1299 | Adeno carcinoma | 1.12 |
| Colon | CXF 280 | Adeno carcinoma, ud | 5.44 |
| Stomach | GXF 214 | Adeno carcinoma, ud | 1.94 |
| Lung, non small | LXFA 1012 | Adeno carcinoma, pd | 1.32 |
| Lung, non small | LXFA 1041 | Adeno carcinoma, md | 1.50 |
| Lung, non small | LXFA 629 | Adeno carcinoma, pd | 1.38 |
| Lung, non small | LXFA 749 | Adeno carcinoma, pd | 1.70 |
| Lung, non small | LXFL 430 | Large cell lung carcinoma, ud | <1.00 |
| Lung, small cell | LXFS 573 | Small cell lung carcinoma | 1.93 |
| Breast | MAXF 1322 | Papillary adeno carcinoma, pd | 1.55 |
| Breast | MAXF 857 | Invasive ductal carcinoma | 1.55 |
| Kidney | RXF 1220 | Hypernephroma, pd | 6.32 |
| Kidney | RXF 423 | Hypernephroid adeno carcinoma | 1.69 | md: moderately differentiated,
pd: poorly differentiated,
ud: undifferentiated

Comparing these values to the results with cell lines (Table 1) it is evident that compound 9 is even more potent against patient-derived tumors than against cell lines.

Example 4

Ability of Compound 9 to Induce a Decrease in the ATP Levels of CT-26 Colon Carcinoma Cells The ability of compound 9 to induce a decrease in the ATP levels of CT-26 colon carcinoma cells was evaluated. It was previously found that the natural jasmonate methyl jasmonate can cause a decrease in ATP levels in cancer cells (Fingrut et al., 2005 Fingrut O, et al. Br. J. Pharmacol. 146:800-808, 2005). However, these experiments were performed under conditions (dosage and length of exposure) at which no cytotoxic effects were evident since dead cells would not contain ATP. The purpose of the present experiments was to evaluate whether a drop in ATP precedes death.

Experimental Set Up

Figure 2:
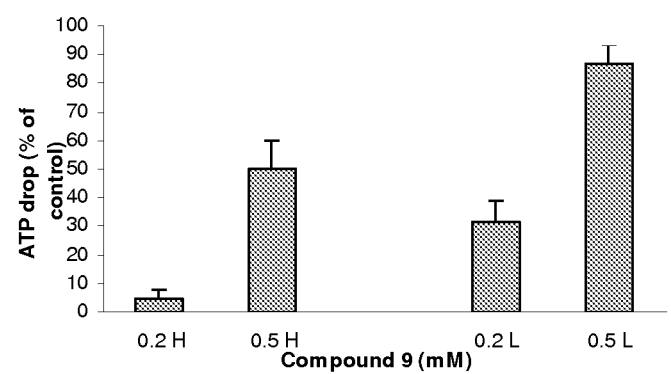
FIG. 2: Shows the ability of compound 9 to induce a decrease in the ATP levels of CT-26 colon carcinoma cells. Drop in ATP level in the cells after 3 hours incubation in different media is plotted; High (28 mM) or low (2 mM) glucose concentration with either low (0.2 mM) or high (0.5 mM) concentration of compound 9 is plotted.

CT-26 cells were exposed to compound 9 for 3 hours and ATP levels were measured using the CellTiter-Glot Luminescent Cell Viability Assay (Promega, Madison, Wis., U.S.A.). As can be seen in FIG. 2, compound 9 induced a significant drop in cellular ATP levels. Furthermore, this effect was decreased in the presence of high glucose levels, suggesting that glycolysis can compensate for the ATP decrease induced by compound 9, again similar to our findings with methyl jasmonate (Fingrut et al, 2005). These data suggest similarities between the mechanism of action of the natural methyl jasmonate and its novel chemical derivative compound 9. It thus appears that a drop in cellular energy levels may precipitate the cytotoxic effect of compound 9.

Example 5

Figure 3A:
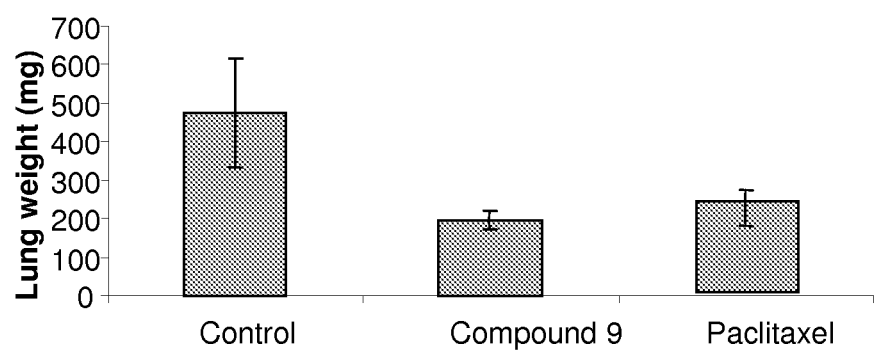
FIG. 3: Shows the ability of compound 9 to decrease experimental metastasis of B16 melanoma cells to the lungs in vivo. A) Lung weight of mice is plotted for a control group of untreated mice, a second group of mice treated with compound 9 and a third group of mice that were treated with Paclitaxel; B) images of the lungs of C57bl mice injected with B16 melanoma cells after being treated for three weeks with compound 9 or paclitaxel (positive control) versus untreated infected mice (negative control).
Figure 3B:
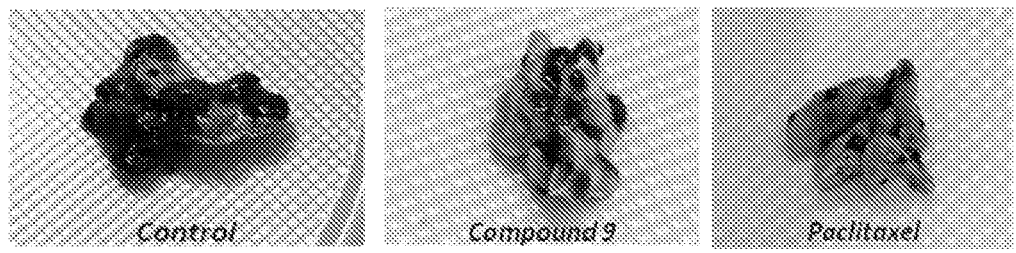

The Ability of Compound 9 to Decrease Experimental Metastasis of B16 Melanoma Cells to the Lungs In Vivo The ability of compound 9 to decrease experimental metastasis of B16 melanoma cells to the lungs in vivo was determined Experimental Set Up The experiment was comprised of 3 groups of C57bl mice (12-15 weeks old, n=12), total of 36 all inoculated with B16F10 melanoma cells, 0.1 ml of B16F10 in PBS×1, inoculums of 7×10$^5$ cells per mouse. Group M1—non treated, Group M2—treated once daily, 5 days a week for 3 weeks with Compound 9 dissolved with surfactants (10 mg/kg, diluted 1:5 with Saline, i.v.), and Group M3—a positive control group treated with Paclitaxel once in 7 days (15 mg/kg, i.v.). After 22 days, mice were sacrificed and lungs were weighed. Lungs with metastases weigh more than normal lungs (which weigh about 200 mg), and a decrease in lung weight in comparison to control tumor-bearing untreated mice signifies an anti-metastatic effect. As can be seen in FIG. 3, compound 9 was very effective in suppressing lung metastasis and at test yielded a P value of 0.000003 for compound 9 versus the control. The data suggest that compound 9 is a very promising new anti-cancer agent.

Example 6

Synthesis

Exemplary synthetic methods for the preparation compounds of the invention are set forth below.

Compound 9:

To a stirred solution of 8-hydroxy quinoline (620 mg, 4.27 mmol) and triethylamine (0.7 mL, 5.12 mmol) in dry THF (20 mL), at 0° C. under argon atmosphere was added dropwise a solution of Jasmonyl chloride (900 mg, 3.94 mmol) in dry THF (20 mL) and the reaction mixture was stirred for 1.5 hr at 0° C., allowed to warm up to room temperature and further stirred for 1 hr. The solvent was then evaporated and the residue diluted with $CH_2Cl_2$ and washed with saturated aq. $NaHCO_3$ (×2). The organic layer was dried over $MgSO_4$ and concentrated in vacuo. The residue was purified by VLC (EtOAc/petroleum ether 1:9) affording compound 9 (728 mg, 55%) as a yellow oil.

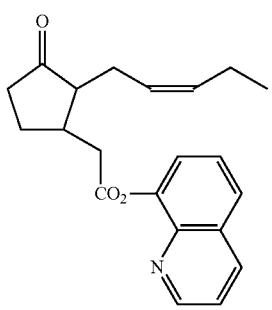

9

Compound 9A:

A mixture of 2.5 g (11.9 mmol) jasmonic acid (i.e. 2-(3-oxo-2-(2-pentenyl)cyclopentyl)acetic acid) and Pd/C (0.5 g) in THF (50 mL) was hydrogenated at room temperature for 4 h. The reaction mixture was filtered and the filtrate was concentrated to give 2-(3-oxo-2-(pentanyl)cyclopentyl)acetic acid (2.5 g, 100%) as yellow oil.

A mixture of 2-(3-oxo-2-(pentanyl)cyclopentyl)acetic acid (1 g, 4.7 mmol), 8-hydroxyquinoline (680 mg, 4.7 mmol), O-(benzotriazol-1-yl)-N,N,N,N-tetramethyluronium hexafluorophosphate (2.12 g, 5.6 mmol, 1.2 eq), triethylamine (950 mg, 9.4 mmol, 2 eq) in THF (50 mL) was refluxed overnight. The reaction mixture was concentrated and the residue was partitioned between ethyl acetate and water. The aqueous layer was extracted with ethyl acetate. The combined organic extracts were dried over $Na_2SO_4$ and concentrated. The residue was purified by prep-HPLC to give compound 9A (400 mg, 25%) as yellow oil.

9A

Compound 11:

A solution of anhydrous D-glucose (159 mg, 0.883 mmol) in pyridine (10 mL) was heated to 100° C. for 1 hr. The solution was allowed to cool to room temperature and a solution of compound 9 (595 mg, 1.76 mmol) in pyridine (10 mL) and NaH (5 mg of 60% NaH in oil, washed with petroleum ether before use, 0.132 mmol). The reaction mixture was heated to 60° C. and stirred for 4 hours. The solvent was then evaporated and the residue diluted with n-butanol and extracted with an aqueous solution of $K_3PO_4$ (0.1N). The organic layer was washed with water containing few drops of AcOH and concentrated in vacuo. The residue was purified by VLC (EtOAc) affording compound 11 (45 mg, 14%) as a yellow oil.

11

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

Example 7

Inhibition of Proliferation of Squamous Cell Carcinoma Cells and Basal Cell Carcinoma In Vitro with Compounds 9 or 9A The effect of methyl jasmonate and compound 9 and 9A on the proliferation of squamous cell carcinoma cells (cell line A431) and basal cell carcinoma cells (cell line TE 354.T) was determined.

Figure 4:
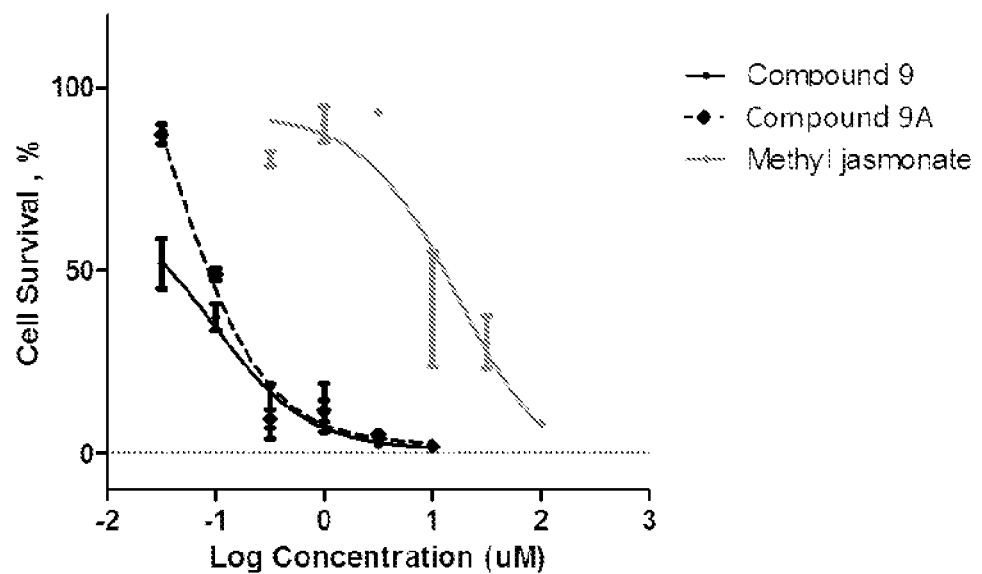
FIG. 4: Shows the ability of compounds 9 and 9A to inhibit cell proliferation of squamous cell carcinoma cells in vitro.

Cells were treated with various concentrations of methyl jasmonate and the compounds 9 and 9A for three days followed by a proliferation assay using XTT reagent (sodium 2,3,-bis(2-methoxy-4-nitro-5-sulfophenyl)-5-[(phenylamino)-carbonyl]-2H-tetrazolium inner salt). As shown in FIG. 4 and table 3, compounds 9 and 9A inhibited the proliferation of squamous cell carcinoma cells with IC50 values of 89 nM and 36 nM, respectively. Methyl jasmonate was shown to be a much less potent inhibitor of squamous cell carcinoma cell proliferation, with IC50 of 14 µM.

Figure 5:
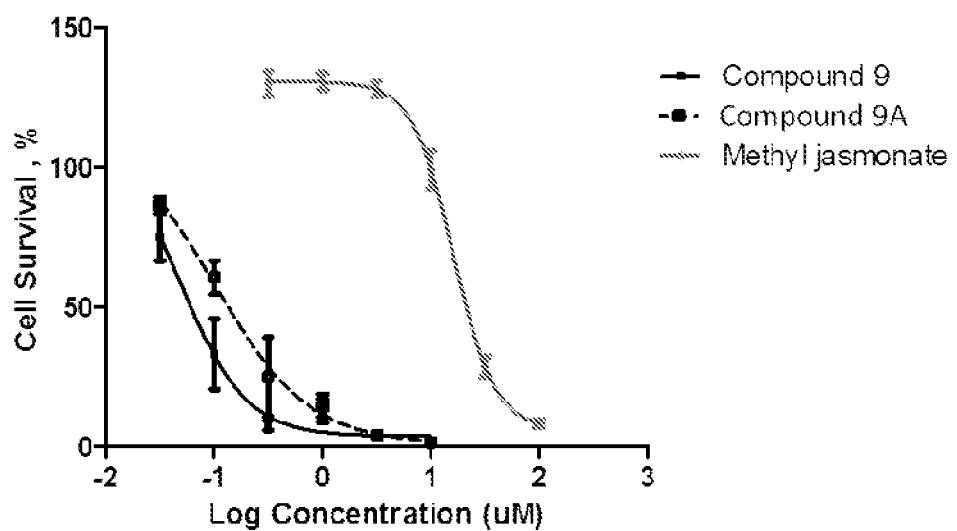
FIG. 5: Shows the ability of compounds 9 and 9A to inhibit cell proliferation of basal cell carcinoma cells in vitro.

As shown in FIG. 5 and table 3, compounds 9 and 9A inhibited the proliferation of basal cell carcinoma cells with IC50 values of 49 nM and 116 nM, respectively. Methyl jasmonate was shown to be a much less potent inhibitor of basal cell carcinoma cell proliferation, with IC50 of 16 µM.

TABLE 3

IC50 values (in nM) for inhibition of cell proliferation by methyl jasmonate, compounds 9 and compound 9A.

| Cell type | Methyl jasmonate | Compound 9 | Compound 9A |
| --- | --- | --- | --- |
| Squamous cell carcinoma cells | 14,000 | 89 | 36 |
| Basal cell carcinoma cells | 16,000 | 49 | 116 |

These results indicate that compounds 9 and 9A are very promising new anti-cancer agents.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

What is claimed is:

1. A compound represented by the structure of Formula II:

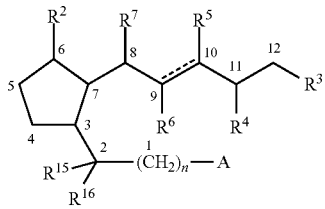

(II)

wherein
A is $COR^1$;
$R^1$ is an unsubstituted or substituted heteroaryloxy;
$R^2$ is oxo;
$R^3$, $R^4$, $R^5$, $R^6$ and $R^7$ are each hydrogen,
wherein the bond between $C_9$ and $C_{10}$ can be a single or double bond;
$R^{15}$ and $R^{16}$ are each hydrogen; and
n is selected from 0, 1 and 2;
including salts, hydrates, solvates, polymorphs, optical isomers, geometrical isomers, enantiomers, diastereomers, and mixtures thereof.

2. The compound of claim 1, wherein $R^1$ is quinolinyloxy.

3. The compound of claim 1, wherein the bond between $C_9$ and $C_{10}$ is a double bond.

4. The compound of claim 1, wherein the bond between $C_9$ and $C_{10}$ is a single bond.

5. The compound of claim 1, which is represented by the structure of Formula 9:

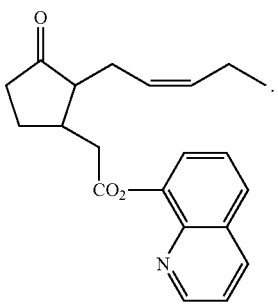

9

6. A pharmaceutical composition comprising a pharmaceutically acceptable carrier, and as an active ingredient the compound according to claim 1.

7. A pharmaceutical composition comprising a pharmaceutically acceptable carrier, and as an active ingredient the compound according to claim 5.

8. The pharmaceutical composition of claim 6, wherein the composition is in a form suitable for topical administration, oral administration, intravenous administration by injection, administration by inhalation, or administration via a suppository.

9. A method for inhibiting cancer cell proliferation, comprising contacting said cancer cells with a therapeutically effective amount of the compound according to claim 1, wherein the cancer cell is selected from the group consisting of: a prostate cancer cell; a breast cancer cell; a colon cancer cell; a lung cancer cell; a lymphoblastic leukemia cell; a kidney cancer cell; a stomach cancer cell; a melanoma cell; a squamous cell carcinoma cell; a basal cell carcinoma cell; a small cell lung carcinoma cell; a non-small cell lung carcinoma cell; and a large cell lung carcinoma cell.

10. A method for inhibiting cancer cell proliferation, comprising contacting said cancer cells with a therapeutically effective amount of the compound according to claim 9, wherein the cancer cell is selected from the group consisting of: a prostate cancer cell; a breast cancer cell; a colon cancer cell; a lung cancer cell; a lymphoblastic leukemia cell; a kidney cancer cell; a stomach cancer cell; a melanoma cell; a squamous cell carcinoma cell; a basal cell carcinoma cell; a small cell lung carcinoma cell; a non-small cell lung carcinoma cell; and a large cell lung carcinoma cell.

11. A method for treating cancer in a subject, comprising administering to the subject having said cancer a therapeutically effective amount of the compound according to claim 1, wherein the cancer is selected from the group consisting of: prostate cancer; breast cancer; colon cancer; lung cancer; lymphoblastic leukemia; lymphoma; kidney cancer; stomach cancer; melanoma; squamous cell carcinoma; basal cell carcinoma; small cell lung carcinoma; non-small cell lung carcinoma; and large cell lung carcinoma.

12. A method for treating cancer in a subject, comprising administering to the subject having said cancer a therapeutically effective amount of the compound according to claim 5, wherein the cancer is selected from the group consisting of: prostate cancer; breast cancer; colon cancer; lung cancer; lymphoblastic leukemia; lymphoma; kidney cancer; stomach cancer; melanoma; squamous cell carcinoma; basal cell carcinoma; small cell lung carcinoma; non-small cell lung carcinoma; and large cell lung carcinoma.

13. The method of claim 12, wherein the cancer is selected from the group consisting of: breast cancer, prostate cancer, stomach cancer, colon cancer, and kidney cancer.

14. The method of claim 12, wherein the cancer is selected from the group consisting of: small cell lung carcinoma, non-small cell lung carcinoma, and large cell lung carcinoma.

15. The method of claim 12, wherein the cancer is selected from the group consisting of: prostate cancer, breast cancer, and colon cancer.

16. The method of claim 12, wherein the cancer is selected from the group consisting of: melanoma, kidney cancer, stomach cancer and colon cancer.

17. The method of claim 12, wherein the cancer is selected from the group consisting of: squamous cell carcinoma, and basal cell carcinoma.

* * * * *